United States Patent
Kinsella

(10) Patent No.: US 11,058,702 B2
(45) Date of Patent: Jul. 13, 2021

(54) METHODS AND COMPOSITIONS FOR THE TREATMENT OF CANCER WITH 5-IODO-2-PYRIMIDINONE-2'-DEOXYRIBOSE (IPDR)

(71) Applicant: EMEK, Inc., Warwick, RI (US)

(72) Inventor: Timothy J. Kinsella, Warwick, RI (US)

(73) Assignee: EMEK, INC., Warwick, RI (US)

( * ) Notice: Subject to any disclaimer, the term of this patent is extended or adjusted under 35 U.S.C. 154(b) by 134 days.

(21) Appl. No.: 16/412,797

(22) Filed: May 15, 2019

(65) Prior Publication Data

US 2020/0069718 A1 Mar. 5, 2020

Related U.S. Application Data

(63) Continuation of application No. 15/475,585, filed on Mar. 31, 2017, now abandoned, which is a continuation of application No. PCT/US2015/054534, filed on Oct. 7, 2015.

(60) Provisional application No. 62/060,688, filed on Oct. 7, 2014.

(51) Int. Cl.
| | |
|---|---|
| A61K 31/505 | (2006.01) |
| A61N 5/10 | (2006.01) |
| A61K 31/7068 | (2006.01) |
| A61K 45/06 | (2006.01) |
| A61K 31/513 | (2006.01) |
| A61K 31/495 | (2006.01) |
| G01N 33/574 | (2006.01) |
| A61K 33/243 | (2019.01) |

(52) U.S. Cl.
CPC ........ *A61K 31/7068* (2013.01); *A61K 31/495* (2013.01); *A61K 31/505* (2013.01); *A61K 31/513* (2013.01); *A61K 33/243* (2019.01); *A61K 45/06* (2013.01); *A61N 5/10* (2013.01); *G01N 33/574* (2013.01); *A61N 2005/1098* (2013.01); *G01N 2800/52* (2013.01)

(58) Field of Classification Search
CPC ...... A61N 5/10–1084; A61N 2005/1085–1098
See application file for complete search history.

(56) References Cited

U.S. PATENT DOCUMENTS

| 5,147,652 A | 9/1992 | Egyud |
| 5,728,684 A | 3/1998 | Cheng et al. |
| 8,716,346 B2 | 5/2014 | Gerson et al. |
| 2003/0229004 A1 | 12/2003 | Zarling et al. |
| 2011/0245304 A1 | 10/2011 | Yen et al. |

FOREIGN PATENT DOCUMENTS

| WO | 92/20816 A1 | 11/1992 |
| WO | 2006/135763 A2 | 12/2006 |
| WO | 2016/044690 A1 | 3/2016 |

OTHER PUBLICATIONS

Goffman et al., "Primary Treatment of Large and Massive Adult Sarcomas With Iododeoxpridine and Aggressive Hyperfractionated Irradiation," Cancer, vol. 67 (1991), p. 572-576. (Year: 1991).*
Blasberg et al., "Imaging Brain Tumor Proliferative Activity with [124I]Iododeoxyuridine," Cancer Research 60:624-635, Feb. 1, 2000.
Boeckman et al., "Cisplatin sensitizes cancer cells to ionizing radiation via inhibition of non-homologous end joining," Mol Cancer Res, May 2005, 3(5):277-285.
The Cancer Genome Atlas (TCGA) Research Network, "Comprehensive genomic characterization defines human glioblastoma genes and core pathways," Nature, Oct. 23, 2008; 455(7216):1061-1068.
Chan et al., "Base excision repair fidelity in normal and cancer cells," Mutagenesis, 21(3):173-178, 2006.
Chang et al., "Conversion of 5-Iodo-2-Pyrimidinone-2'-Deoxyribose to 5-Iodo-Deoxyuridine by Aldehyde Oxidase," Biochemical Pharmaclogy, 43(10):2269-2273, 1992.
Chapman et al., "Ribonucleotide reductase inhibitors: a new look at an old target for radiosensitization," Frontiers in Oncology, vol. 1, Article 56, pp. 1-6, Jan. 2012.
Chi et al., Iododeoxyuridine Chemosensitization of cis-Diamminedichloroplatinum (II) in Human Bladder Cancer Cells, Cancer Research 54:2701-2706, May 15, 1994.
Cook et al., "Measurement of Thymidine Replacement in Patients with High Grade Gliomas, Head and Neck Tumors, and High Grade Sarcomas after Continuous Intravenous Infusions of 5-Iododeoxyuridine," Cancer Research 52:719-725, Feb. 1, 1992.
Dupertuis et al., "Unlabelled iododeoxyuridine increases the rate of uptake of [125I]iododeoxyuridine in human xenografted glioblastomas," European Journal of Nuclear Medicine, 29(4):499-505, Apr. 2002.
Eckert et al., "Definitive radiotherapy and Single-Agent radiosensitizing Ifosfamide in Patients with localized, irresectable Soft Tissue Sarcoma: A retrospective analysis," Radiation Oncology 2010, 5(55):1-6.
Eisbruch et al., "Bromodeoxyuridine Alternating With Radiation for Advanced Uterine Cervix Cancer: A Phase I and Drug Incorporation Study," Journal of Clinical Oncology, 17(1):31-40, 1999.
Epstein et al., Treatment of Locally Advanced Cancer of the Head and Neck With 5'-Iododeoxyuridine and Hyperfractionated Radiation Therapy: Measurement of Cell Labeling and Thymidine Replacement, Journal of the National Cancer Institute, 86(23):1775-1780, Dec. 7, 1994.
Fisher et al., "Phase 2 Study of Temozolomide-based Chemoradiation Therapy for High-risk Low-grade Gliomas: Preliminary Results of Radiation Therapy Oncology Group 0424," Int J Radiat Oncol Biol Phys, Mar. 1, 2015, 91(3):497-504.
Fokas et al., "Tumor Regression Grading After Preoperative Chemoradiotherapy for Locally Advanced Rectal Carcinoma Revisited: Updated Results of the CAO/ARO/AIO-94 Trial," Journal of Clinical Oncology, 32(15):1554-1562, May 20, 2014.

(Continued)

*Primary Examiner* — Thaddeus B Cox
(74) *Attorney, Agent, or Firm* — K&L Gates LLP

(57) ABSTRACT

Provided are methods of treating a human patient having cancer by administering IPdR to the patient in the form of an oral drug and administering radiation therapy (RT) to the patient. The method can also include administering a chemotherapeutic drug or biologic agent to the patient. Also provided are methods for optimizing IPdR sensitization for radiation therapy for a cancer patient having been administered IPdR.

15 Claims, No Drawings

(56) References Cited

OTHER PUBLICATIONS

Gurkan et al., "Probabilistic Modeling of DNA Mismatch Repair Effects on Cell Cycle Dynamics and Iododeoxyuridine-DNA Incorporation," Cancer Res 2007; 67(22):10993-1000.
Gurkan et al., "Quantitative analysis of the effects of iododeoxyuridine and ionising radiation treatment on the cell cycle dynamics of DNA mismatch repair deficient human colorectal cancer cells," IET Syst. Biol., 2013, 7(4):114-124.
Kinsella, "An Approach to the Radiosensitization of Human Tumors," The Cancer Journal from Scientific American, 1996, 2(4):184-193.
Kinsella, Coordination of DNA Mismatch Repair and Base Excision Repair Processing of Chemotherapy and Radiation Damage for Targeting Resistant Cancers, American Association for Cancer Research, 2009, 7 pages.
Kinsella, "Chapter 7—DNA Mismatch Reapir: Its Role in Human Carcinogenesis and as a Predictive and/or Prognostic Biomarker for Cancer Therapy," DNA Repair and Cancer: From Bench to Clinic, 2013, pp. 195-232.
Kinsella et al., "Toxicology and pharmacokinetic study of orally administered 5-iodo-2-pyrimidinone-2' deoxyribose (IPdR) x 28 days in Fischer-344 rats: impact on the initial clinical phase I trial design of IPdR-mediated radiosensitization," Cancer Chemother Pharmacol (2008) 61:323-334.
Kinsella et al., An in Vivo Comparison of Oral 5-Iodo-2'-deoxyuridine and 5-Iodo-2-pyrimidinone-2'-deoxyribose Toxicity, Pharmacokinetics, and DNA Incorporation in Athymic Mouse Tissues and the Human Colon Cancer Xenograft, HCT-116, Cancer Research 54, 2695-2700, May 15, 1994.
Kinsella et al., Preclinical Evaluation of 5-Iodo-2-pyrimidinone-2'-deoxyribose as a Prodrug for 5-Iodo-2'-deoxyuridine-mediated Radiosensitization in Mouse and Human Tissues, Clinical Cancer Research, 4:99-109, Jan. 1998.
Kinsella et al., "Preclinical Toxicity and Efficacy Study of a 14-day Schedule of Oral 5-Iodo-2-pyrimidinone-2'-deoxyribose as a Prodrug for 5-Iodo-2'-deoxyuridine Radiosensitization in U251 Human Glioblastoma Xenografts," Clinical Cancer Research, 6:1468-1475, Apr. 2000.
Kinsella et al., "Preclinical Study of the Systemic Toxicity and Pharmacokinetics of 5-Iodo-2-deoxypyrimidinone-2'-deoxyribose as a Radiosensitizing Prodrug in Two, Non-Rodent Animal Species: Implications for Phase I Study Design," Clinical Cancer Research, 6:3670-3679, Sep. 2000.
Kinsella et al., "Integration of principles of systems biology and radiation biology: toward development of in silico models to optimise IUdR-mediated radiosensitization of DNA mismatch repair-deficient (damage tolerant) human cancers," Frontiers in Oncology, Aug. 2011 vol. 1, Article 20, pp. 1-20.
Kinsella et al., "5-iodo-2-pyrimidinone-2'-deoxyribose (IPdR)-mediated cytotoxicity and radiosensitization in U87 human glioblastoma xenografts," Int J Radiat Oncol Biol Phys, Nov. 15, 2007, 69(4):1254-1261.
Kinsella, "Understanding DNA Damage Response and DNA Repair Pathways: Applications to More Targeted Cancer Therapeutics," Seminars in Oncology, vol. 36, No. 2, Suppl. 1, Apr. 2009, pp. S42-S51.

Krishnamurthi et al., "Adjuvant Therapy for Rectal Cancer," Clinics in Colon and Rectal Surgery, 20(3):167-181, 2007.
Kummar et al., "First-in-Human Phase 0 Trial of Oral 5-iodo-2-pyrimidinone-2'-deoxyribose (IPdR) in Patients with Advanced Malignancies," Clin Cancer Res, Apr. 1, 2013, 197(7):1852-1857.
Lawrence et al., "Milestones in the Use of Combined-Modality Radiation Therapy and Chemotherapy," Journal of Clinical Oncology, 32(12):1173-1179, Apr. 20, 2014.
Lindstrom et al., "Global Comparison of Radiation and Chemotherapy Dose-Response Curves with a Test for Interaction," Radiation Research, 135(2):269-277, Aug. 1993.
Miller et al., "Effects of 5'-Aminothymidine and Leucovorin on Radiosensitization by Iododeoxyuridine in Human Colon Cancer Cells," Clinical Cancer Research, 1:407-416, Apr. 1995.
Moding et al., "Strategies for optimizing the response of cancer and normal tissues to radiation," Nat Rev Drug Discov, Jul. 2013, 12(7):526-542.
Perry et al., "Dissecting DNA repair in adult high grade gliomas for patient stratification in the post-genomic era," Oncotarget, 5(14):5764-5781, 2014.
Saif et al., "IPdR: a novel oral radiosensitizer," Expert Opin. Investig. Drugs, 16(9):1415-1424, 2007.
Seo et al., "Differential Radiosensitization in DNA Mismatch Repair-Proficient and -Deficient Human Colon Cancer Xenografts with 5-Iodo-2-pyrimidinone-2'-deoxyribose," Clinical Cancer Research, 10:7520-7528, Nov. 15, 2004.
Seo et al., "Schedule-Dependent Drug Effects of Oral 5-Iodo-2-Pyrimidinone-2'-Deoxyribose as an In vivo Radiosensitizer in U251 Human Glioblastoma Xenografts," American Association for Cancer Research, 2005. doi:10.1158/1078-0432.CCR-05-1138, 9 pages.
Speth et al., "Iododeoxyuridine (IdUrd) Incorporation into DNA of Human Hematopoietic Cells, Normal Liver and Hepatic Metastases in Man: As a Radiosensitizer and as a Marker for Cell Kinetic Studies," Int. J. Radiation Oncology Biol. Phys., 16:1247-1250, 1989.
Stupp et al., "Effects of radiotherapy with concomitant and adjuvant temozolomide versus radiotherapy alone on survival in glioblastoma in a randomised phase III study: 5-year analysis of the EORTC-NCIC trial," Lancet Oncol 2009, 10:459-466.
Taverna et al., "Inhibition of Base Excision Repair Potentiates Iododeoxyuridine-induced Cytotoxicity and Radiosensitization," Cancer Research, 63:838-846, Feb. 15, 2003.
Taverna et al., Methoxyamine potentiates DNA single strand breaks and double strand breaks induced by temozolomide in colon cancer cells, Mutation Research 485:269-281, 2001.
PCT Notification Concerning Transmittal of International Preliminary Report on Patentability (Chapter 1 of the Patent Cooperation Treaty) for International Application No. PCT/US2015/054534, dated Apr. 20, 2017, 9 pages.
Goffman et al., "Primary Treatment of Large and Massive Adult Sarcomas With Iododeoxpridine and Aggressive Hyperfractionated Irradiation," Cancer 67:572-576 (1991).
Dianov, "Base excision repair targets for cancer therapy," Am. J. Cancer Res. 1(7):845-851 (2011).
Chang et al., "Conversion of 5-Iodo-2-Pyrimidinone-2'-Deoxyribose to 5-Iodo-Deoxyuridine by Aldehyde Oxidase", Biochemical Pharmacology, May 28, 1992, pp. 2269-2273, vol. 43, No. 10.

* cited by examiner

METHODS AND COMPOSITIONS FOR THE TREATMENT OF CANCER WITH 5-IODO-2-PYRIMIDINONE-2'-DEOXYRIBOSE (IPDR)

REFERENCE TO RELATED APPLICATIONS

This continuation application claims priority to U.S. application Ser. No. 15/475,585, filed Mar. 31, 2017, which continuation application claims priority to and the benefit of U.S. Provisional Application No. 62/060,688, filed Oct. 7, 2014, and PCT Application No. PCT/US2015/054534 filed Oct. 7, 2015, the entire contents of each of which are hereby incorporated by reference herein.

REFERENCE TO FEDERAL FUNDING

This invention was made with government support under: RO1 CA 50595 awarded by the National Institutes of Health and the National Cancer Institute; R44 CA 76835 awarded by the National Institutes of Health; RAID #197 awarded by the National Cancer Institute; and HHSN261201400013C awarded by the National Cancer Institute. The government has certain rights in the invention.

FIELD OF THE INVENTION

The invention relates to methods and compositions for treating cancer. In particular, the invention relates to methods and compositions for treating cancer by administering 5-iodo-2-pyrimidinone-2'-deoxyribose (IPdR) to a patient in need thereof.

BACKGROUND

In 2015, it was estimated that 1,658,370 men and women in the U.S. would be diagnosed with cancer, and nearly 590,000 cancer patients would die of their disease. Currently, cancer is the second leading cause of death in the U.S. and is projected to surpass the death rate from heart disease in the next few years.

Radiation therapy (RT) plays a critical role in the treatment of most common human cancers, with over 50% of all cancer patients receiving RT at some point during the course of their treatment. It is estimated that over 40% of cured cancer patients have received RT as part of their cancer treatment (http://www.rtanswers.org/statistics/aboutradiationtherapy). Consequently, any invention that improves the efficacy and/or reduces the toxicity profile of RT will have a profound impact on cancer treatment in the U.S. and worldwide.

RT kills cells via several biological and molecular mechanisms, some of which are well understood, while others need further elucidation. RT does not kill only cancer cells, but can also kill normal cells within the RT treatment volume in a patient, leading to both acute (occurring during or immediately following RT) and late (occurring months to years following RT) normal tissue toxicities. In principle, all cancers can be controlled if sufficiently high radiation doses can be delivered to tumor cells; however, in practice, the radiation dose is frequently limited by toxicities resulting from exposure of normal tissues to high radiation doses. The balance between the probability of tumor control and the risk of normal tissue complications is a measure of the therapeutic index (TI). Normal tissue damage cannot be completely avoided because the radiation doses necessary to achieve tumor control typically overlap with those that can cause acute and/or late normal tissue toxicities. The goal, therefore, is to develop strategies that can selectively increase the radiation effect on the tumor while sparing the normal cells and tissues.

A major RT strategy employed to achieve this goal is to target defined volumes of cancerous tissue while attempting to minimize RT exposure to adjacent normal tissues. Over the last 3 decades, there have been significant improvements in our technical capabilities to better target tumor tissues and limit RT exposure to normal tissues by utilizing technologies such as 3-dimensional conformal RT, intensity-modulated RT, image-guided RT as well as the more costly proton beam RT and heavy ion RT. However, significant RT dose limiting acute and late normal tissue toxicities are observed in clinical testing of these new technologies with the use of modest RT dose escalations. Indeed, two recent reviews conclude that the tumor control probability of these new RT technologies for common cancers such as rectal cancer, high-grade gliomas, and head and neck cancer will be increased by <10% at best.

So, target refinement as a strategy to improve the efficacy and/or toxicity of RT has led to only limited improvements.

Another strategy has been to use systemic cytotoxic chemotherapy in conjunction with RT in an attempt to further improve tumor control. In addition to the direct killing of the cancer cells by the drug, some of these agents have been observed to enhance the killing effects of RT when the two modalities are administered together. Currently, cytotoxic chemotherapy drugs such as 5-fluorouracil (5-FU), capecitabine (a 5-FU prodrug), cisplatinum, carboplatinum, and to a lesser extent, mitomycin-C, gemcitabine, irinotecan, taxol, oxaliplatinum and temozolomide are used as potential clinical radiosensitizers for a large number of common cancers including rectal cancer (42,000 new cases), lung cancer (228,000 new cases), head and neck cancers (41,000 new cases), pancreas cancer (45,000 new cases), anal cancer (7,000 new cases) and high grade brain cancers (14,000 new cases), based on 2015 cancer incidence data. Less commonly, biologics such as the humanized monoclonal antibodies cetuximab (targeting the epidermal growth factor receptor) and bevacizumab (targeting the vascular endothelial growth factor receptor) are used during RT either alone or in combination with some of the above cytotoxic chemotherapy drugs. However, none of these drugs or biologics were developed as specific clinical radiosensitizers and all have significant single agent acute and late normal tissue toxicities, which can be further enhanced when used during RT. It is now clear that most currently used concomitant chemo/biologic-RT combinations are delivered close to (or at) the limits of normal tissue tolerances such that further intensification by increasing the cytotoxic drug dose or by adding different classes of cytotoxics or biologics appears not to be a viable treatment strategy for these common cancers.

A third strategy to improve the efficacy/toxicity profile of RT is to use a drug(s) that specifically targets mechanisms of tumor cell resistance to RT, thereby making the tumor more susceptible to the damaging effects of RT relative to the normal tissues. While it is an appealing strategy, there are currently no drugs with a specific Federal Drug Administration (FDA) or European Medicines Agency (EMA) approved indication of radiosensitization. However, it is well recognized that the primary cellular target of RT is DNA. RT kills cells by causing irreversible DNA strand breaks, making them unable to divide and proliferate. Well over 50 years ago, it was recognized that certain drugs, called halogenated nucleoside analogs, are falsely incorporated into DNA, and when these cells with the defective DNA are exposed to RT, tumor cell killing is increased by up to two-three fold compared to cells without the defective DNA. To date, the nucleoside analog that has been found to be the most effective as a specific radiosensitizing drug is 5-iodo-2'-deoxyuridine (IUdR). Clinical trials during the 1990's-early 2000's showed that IUdR enhanced the effectiveness of RT in the treatment of RT-resistant brain and soft tissue/bone cancers (summarized in Tables 1 and 2). However, the use of IUdR is completely impractical; that is, it needs to be administered as a continuous intravenous infusion, 24 hours/day for 5-6 weeks during RT. Prolonged IUdR infusions also caused systemic normal tissue toxicities, especially myelosuppression and GI toxicities. Consequently, Phase III clinical trials were not performed and IUdR is not approved for clinical use.

More recently, a newer nucleoside analog, 5-iodo-2-pyrimidinone-2'-deoxyribose (IPdR) has been developed. IPdR is taken by mouth (po) and is a prodrug of IUdR, that is, when IPdR is ingested, the body converts it into IUdR, so IPdR is essentially a way to conveniently administer a drug, IUdR, that is known to enhance the effectiveness of RT. IPdR has thus been specifically developed as a radiosensitizing drug; this development having been sponsored by the National Cancer Institute (NCI) through a series of extramural and intramural grants over two decades. The rigid guidelines for the preclinical and early phase clinical assessment of novel radiosensitizers like IPdR have been published by the Radiation Modifier Working Group of the U.S. NCI, as well as by the UK National Cancer Research Institute (NCRI). The extensive preclinical studies of IPdR passed the rigid guidelines from both the U.S. NCI and UK NCRI Working Groups, as well as the U.S. FDA, leading to the filing of an Investigational New Drug (IND) submission. Importantly, po IPdR was found to be more effective as a tumor radiosensitizing drug in animals with little normal tissue toxicities when directly compared to continuous intravenous infusions of IUdR. Most recently (April, 2013), intramural NCI investigators published the first-in-human Phase 0 trial of single doses of po IPdR in patients with advanced malignancies. This study concluded that adequate plasma levels of the active drug, IUdR, from the oral prodrug, IPdR, were achieved, justifying proceeding with a Phase I trial of IPdR in combination with radiation. Indeed, the U.S. NCI is currently sponsoring two Phase I and Pharmacokinetic (PK) trials combining escalating doses of IPdR given orally, once daily×28 days during RT for patients with metastatic gastrointestinal cancers, and for patients with brain metastases.

SUMMARY OF THE INVENTION

The present invention relates, in part, to the use of IPdR as a radiosensitizing drug for treating cancer patients. The present invention also relates, in part, to assays that correlate IUdR-DNA cellular incorporation in tumors and normal tissues to improve the therapeutic index (TI) for IPdR and RT combination therapy and to identify groups of patients that may benefit from the use of IPdR and RT.

The present invention generally relates to the use of 5-iodo-2-pyrimidinone-2'-deoxyribose (IPdR), an oral (po) prodrug of 5-iodo-2'-deoxyuridine (IUdR), used during radiation therapy (RT) to maximally enhance IUdR-mediated tumor radiosensitization while minimizing normal tissue toxicities, resulting in an improved therapeutic index (TI). In various embodiments, the methods and compositions of the invention are used to treat "difficult to cure" human solid cancers, including cancers with genetic/epigenetic deficiencies in DNA mismatch repair (MMR) and/or base excision repair (BER). This invention also relates to the clinical development of po IPdR used during RT+specific chemotherapy combinations, particularly fluoropyrimidines, platinum analogs, temozolomide, and ribonucleotide reductase inhibitors, to maximally enhance IUdR-mediated tumor chemo- and radio-sensitization resulting in an improved TI for the combined modality treatment in solid cancers where use of those chemotherapeutic agents are indicated.

Additionally, the invention involves the development of assays that will allow assessment of the radiosensitization effect of IPdR, and specifically, the use of those assays to predict disease response in individuals or groups of patients. In some embodiments, these assays involve cellular measurements of % IUdR-DNA incorporation in tumor cells and in potential IUdR-dose-limiting normal tissue cells that, when measured in combination, may provide an intermediate prediction of TI (i.e. efficacy and toxicity) during po IPdR+RT treatment.

In one aspect, the invention provides methods of treating a human patient having cancer. The method includes the steps of administering IPdR to the patient in the form of an oral drug; and administering radiation therapy (RT) to the patient. These methods are particularly useful if a patient cannot tolerate the optimum, or standard of care, levels of radiation treatment without the addition of IPdR. These methods also are particularly suitable for treating sporadic MMR-deficient cancers.

In another aspect, the invention provides methods of treating a human patient having cancer that include the steps of administering IPdR to the patient in the form of an oral drug; administering a chemotherapeutic drug or biologic agent to the patient; and administering radiation therapy (RT) to the patient. These methods are particularly suitable for treating BER-deficient cancers.

In another aspect, the invention provides methods for optimizing IPdR sensitization for radiation therapy for a cancer patient having been administered IPdR. These methods include the steps of determining an IUdR-DNA incorporation level in a first tumor biopsy taken from the patient; determining an IUdR-DNA incorporation level in a normal tissue sample; and calculating a therapeutic index; wherein the therapeutic index guides dose and schedule of radiation therapy. In various embodiments, the therapeutic index is calculated by dividing the percent IUdR-DNA incorporation level in the first tumor biopsy by the percent IUdR-DNA incorporation of the normal tissue sample. In various embodiments, the tumor biopsy and normal tissue sample are obtained from the same patient, and in some embodiments the samples are obtained prior to administering radiation therapy. In various embodiments, IUdR-DNA incorporation levels are measured by high performance liquid chromatography (HPLC) or flow cytometry (e.g., using anti-IUdR antibodies). In various embodiments, the method includes the step of determining an IUdR-DNA incorporation level in a second tumor biopsy taken at a second time from the patient, determining an IUdR-DNA incorporation level in a normal tissue sample; and calculating a therapeutic index. In various embodiments, the normal tissue sample includes circulating cells (e.g., granulocytes) or oral mucosa. The tumor biopsies and tissue samples can be obtained at periodic intervals, such as weekly or monthly intervals.

Embodiments of any of the foregoing aspects can include one or more of the following steps or features:

In various embodiments, radiation therapy is administered in a therapeutically effective amount. Radiation therapy can be delivered using a hyperfractionated technique. In addition, the radiation therapy can be delivered using one or more of the following techniques: 3-dimensional conformal radiation therapy, intensity-modulated radiation therapy, image-guided radiation therapy, tomotherapy, stereotactic radiosurgery and stereotactic body radiation therapy. The source of radiation therapy can be any suitable source, such as, for example, protons and carbon ions.

In various embodiments, a therapeutically effective amount of a chemotherapeutic drug or biologic agent is administered or provided to the patient. The chemotherapeutic drug can be a fluoropyrimidine, such as, by way of non-limiting example, 5-fluorouracil, floxuridine, capecitabine, DPD-inhibiting fluoropyrimdines, and combinations thereof. The chemotherapeutic drug can be a platinum analog such as, by way of non-limiting example, cisplatinum, carboplatinum, oxaliplatinum, and combinations thereof. The chemotherapeutic drug can be a ribonucleotide reductase inhibitor, such as, by way of non-limiting example, hydroxyurea, gemcitabine, triapine, COH29, and combinations thereof. The chemotherapeutic drug also can be a methylating agent or a MMR modulator. The biologic agent can be, for example, a BER modulator.

In various embodiments, the cancer or tumor is a solid tumor.

In various embodiments, IPdR is administered at a dose of 0.1-50 gm/M2/day, and more preferably between 2-5 gm/M2/day. For example, IPdR can be administered at a dose of about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6, 7, 8, 9, 10, 15, 20, 25, 30, 35, 40, 45, or 50 gm/M2/day, and any range or value between about 0.1-50 gm/M2/day.

DETAILED DESCRIPTION

To facilitate understanding of the invention, a number of terms are defined below.

A radiosensitizer (or radiation sensitizer) is a drug or compound that is capable of being incorporated into cellular DNA and subsequently enhances the DNA damage caused by ionizing radiation (IR) when human solid cancers are treated with radiation therapy (RT). 5-iodo-2'-deoxyuridine (IUdR) is an analog of thymidine (TdR) that is readily taken up by cells via active nucleoside transport and is initially phosphorylated to the monophosphate derivative (IdUMP) by the rate-limiting enzyme, thymidine kinase (TK). IdUMP is sequentially phosphorylated intracellularly to the triphosphate derivative, IdUTP, which is then used in DNA replication, in direct competition with deoxythymidine triphosphate (dTTP), by DNA polymerase. TdR replacement by IUdR results from stereochemical similarities between the Van der Waal's radius of the iodine atom (2.15 Angstrom) and the methyl group (2.0 Angstrom) at the 5-position of the uridine molecule. IUdR is not efficiently absorbed when administered orally; therefore, requiring intravenous (IV) or intra-arterial (IA) administration. Unfortunately, the plasma half-life of IV or IA IUdR is <5 minutes, with rapid catabolism of the drug, principally by the liver, to the free base, followed by dehalogenation. Consequently, prolonged infusions of IUdR are necessary for it to be effective as a clinical radiosensitizer.

A prodrug is a compound that, upon administration, must undergo chemical conversion by metabolic processes before becoming an active pharmacological agent. Prodrugs are often designed to improve bioavailability when the active drug itself is poorly absorbed from the gastrointestinal tract. With respect to the present invention, 5-iodo-2-pyrimidinone-2'-deoxyribose (IPdR) is a prodrug of IUdR with excellent bioavailability when administered orally in non-human species (mice, rats, ferrets and monkeys) as well as in humans. An aldehyde oxidase, principally in liver, efficiently converts IPdR to IUdR.

Similarly, the active drug, IUdR or it's oral prodrug, IPdR, may also enhance the cytotoxicity of several different clinically relevant cancer chemotherapy drugs, and as such, can be classified as a chemosensitizer (or chemotherapy modifying drug). The interaction of IUdR (or IPdR) with these cancer chemotherapy drugs can be quantified experimentally using biostatistical methodologies as defined below. Such chemotherapy drug+IR+IPdR combinations are disclosed herein.

The evaluation of the present invention in pre-clinical studies of IPdR as an in vivo radiosensitizer and IUdR as an in vitro radiosensitizer and chemosensitizer required biostatistical tests of interaction, i.e. less than additive (antagonistic), additive, or greater than additive (synergistic) effects of IR±IUdR (or IPdR) and chemotherapy drug/biologic±IUdR (or IPdR). For the in vitro studies using clonogenic survival data of human cancer cells, the response of interest is not a single value, but rather a dose-response relationship or curve (over some defined range of doses). A radiation cell survival curve is a dose-response relationship between the ionizing radiation (IR) dose applied to cells and the proportion of cells surviving the IR exposure. A chemotherapy cell survival curve is a similar relationship between the dose of a chemotherapy agent (drug/biologic) and cell survival.

Alternatively, other biostatistical methodologies can be used in experimental in vitro (cellular) or in vivo (animals; typically, athymic mice with human cancer tumor xenografts) assays to measure synergistic (greater than additive) effects of IUdR or IPdR and IR or modifiers of IR-induced DNA damage repair. Additionally, computational in silico models have been developed and used to quantitatively analyze the effects of DNA Mismatch Repair (MMR) and Base Excision Repair (BER) processing of IUdR-DNA cellular incorporation on the effectiveness of the pre-clinical treatment strategies where IUdR (or IPdR) and/or IR are used. These in silico models of the two different DNA repair processes (i.e. MMR and BER) have been developed at both the cellular level and the molecular level. The MMR status and the BER status of both normal and human cancer cells/tissues are important for determining the % IUdR-DNA cellular incorporation, the cell cycle response to different levels of % IUdR-DNA cellular incorporation, as well as the cytotoxic (cell death) response to IPdR+IR. The results of these extensive pre-clinical in vitro, in vivo, and in silico modelings have served as important milestones leading to the current human clinical development of IPdR as disclosed herein.

Pharmacokinetic (PK) studies are intended to define the time course of a drug and, where appropriate, major metabolite concentrations in plasma. In studies needed to support a future New Drug Application (NDA) from the Federal Drug Administration (FDA) for a prodrug such as IPdR, critical information for the application will be the rate of drug absorption of IPdR by measuring plasma levels, the rate of conversion of IPdR to IUdR using plasma measurements, and the rate of elimination of IPdR, IP, IUdR and IU by metabolic and excretory processes. As IPdR is designed to be given at least once daily over a period of several weeks during RT or combined RT and chemotherapy (chemoRT), detailed analyses of changes in PK parameters with the dosing schedule and duration of dosing will be necessary to attempt to maximize tumor radio-(or chemo-) sensitization and/or minimize normal tissue toxicities. Additionally, PK information regarding demographic characteristics (age, sex, race), external factors (e.g. meals or other drug-drug PK interactions), and use in specific cancer patient populations (e.g. high-grade gliomas, head and neck cancers, rectal cancers) will be collected in the clinical testing of IPdR. Detailed PK studies in several animal species were completed for FDA IND approval.

Extraction from the plasma and subsequent analysis by high performance liquid chromatography (HPLC) of IPdR and its major metabolite, 5-iodo-2-pyrimidinone (IP), and of IUdR and its major metabolite, 5-iodouracil (IU), have been described by Kinsella, et al. An in vivo comparison of oral 5-iodo-2'-deoxyuridine and 5-iodo-2-pyrimidinone-2'-deoxyribose toxicity, pharmacokinetics, and DNA incorporation in athymic mouse tissues and the human colon cancer xenograft, HCT-116. Cancer research. 1994; 54(10):2695-700. These nucleoside analogs are extracted from the plasma by the addition of 5-chloro-2'-deoxyuridine (internal standard) and acetonitrile. The samples are redissolved in deionized water for HPLC analysis using a Spectra-Physics P2000 pump and UV2000 detection (Spectra-Physics Analytical, Fremont, Calif.) on a 3.9×300 mm µ Bondapak C18 reverse phase column (Waters Associates, Milford, Mass.). Peaks are detected at 335 mm (IPdR and IP) and 290 mm (IUdR and IU) versus authentic standards. Typical retention times for IPdR, IP, IUdR, and IU were 21.9, 14.0, 14.4, and 8.3 minutes, respectively. Seventy percent recovery of the nucleoside analogs is achieved using this method for all in vivo studies of IPdR prior to 2008. Since that time, a more sensitive assay of these plasma nucleosides has been established using liquid chromatography with tandem mass spectrometry (LC-MS/MS) (Agilent Technologies, Santa Clara, Calif.) with the lower limits of quantitation of 0.1 µmol/L for IUdR and IPdR, and 0.25 µmol/L for IU and IP, as described by Kinsella et al., "Toxicology and pharmacokinetic study of orally administered 5-iodo-2-pyrimidinone-2'deoxyribose (IPdR)×28 days in Fischer-344 rats: impact on the initial clinical phase I trial design of IPdR-mediated radiosensitization," Cancer Chemother Pharmacol. 2008; 61(2):323-34. This more sensitive assay will be used in the proposed human clinical trials described in this invention. A sensitive liquid chromatography coupled with tandem mass spectrometry detection (LC/MS-MS) method can be used to measure plasma concentrations of IPdR, IdUrd, and other metabolites. Plasma samples are processed by solvent deproteinization. Separation of IPdR and its metabolites can be conducted on an Agilent 1200LC system (Agilent Technologies) using a 4.6×250 mm Synergi Hydro-RP C18 column. All solvents should be high-pressure liquid chromatography (HPLC) grade. All other reagents will also be obtained from the Sigma-Aldrich Company. Calibration curves will be constructed by adding known amounts of IPdR, IP, IdUrd, and IUra to control human plasma to give samples containing concentrations ranging 0.1 to 50 mmol/L of each compound. The response factor is linear over the range of 0.1 to 50 mmol/L. Samples will be diluted 1:10 in control matrix and reanalyzed when calculated concentrations exceed 50 mmol/L. Kumar et al., "First-in-human phase 0 trial of oral 5-iodo-2-pyrimidinone-2'-deoxyribose in patients with advanced malignancies," Clinical Cancer Research 2013; 19(7):1852-57.

In the prior clinical Phase I and II trials of continuous intravenous infusions of IUdR+RT for high-grade gliomas (Table 1), high-grade sarcomas (Table 2), in patients with liver metastases for colorectal cancer, and in patients with head and neck cancers, the % IUdR-DNA cellular incorporation was measured in tumor tissue as well as normal tissues, including normal liver and in circulating blood cells (granulocytes). In general, the % IUdR-DNA cellular incorporation in tumors and normal tissues correlated with the duration of the continuous IUdR infusions. In a clinical study of prolonged (28 days) continuous intravenous infusions, the % IUdR-DNA cellular incorporation in circulating granulocytes predicted for IUdR-mediated myelosuppression. In the pre-clinical studies comparing continuous IUdR infusions+RT and daily po IPdR+RT, the % IUdR-DNA cellular incorporation was measured in human tumor xenografts, as well as in two normal tissues (bone marrow and bowel epithelium). Using % IUdR-DNA cellular incorporation as a surrogate of tumor radiosensitization in the xenografts and as a surrogate of normal tissue toxicity (e.g. weight loss, myelosuppression), it was found that IPdR was a more effective radiosensitizer and was associated with less normal tissue systemic toxicities compared to continuous infusion IUdR. This invention validates this surrogate (i.e. % IUdR-DNA cellular incorporation) as a measure of the TI of IPdR.

Two standard laboratory techniques (flow cytometry and high performance liquid chromatography) have been established to measure the % IUdR-DNA cellular incorporation in tumor cells and normal cells, including cells from the bone marrow, gastrointestinal epithelium, and circulating granulocytes. Flow cytometry is a laser-based, biophysical technology employed for marker detection (i.e. IUdR-DNA cellular incorporation) by suspending cells in a stream of fluid and passing them by an electronic detection apparatus. Fluorescence-activated-cell-sorting (FACS) (Becton-Dickinson, Mountain View, Calif.) is a specialized type of flow cytometry that allows for sorting a heterogeneous mixture of cells (e.g. cells with or without IUdR-DNA incorporation) based on the specific light scattering and fluorescence characteristics of each cell. To measure the proportion of cells "labeled" (i.e. with a defined % IUdR-DNA incorporation level) following an exposure to IPdR, the tumor and normal tissue/cells from the patient are obtained by needle biopsy (or phlebotomy for circulating granulocytes) and processed by mechanical mincing and pepsin digestion for tumor specimens, or Ficoll-Hypaque isolation followed by a Histopaque density gradient (Sigma Chemical Co., St Louis, Mo.) for granulocytes, to obtain a single-cell suspension. After fixing the single-cell suspension with 70% ethanol in normal saline, the DNA is partially denatured with 2N HCl and subsequently reacted with a mouse anti-IUdR monoclonal antibody (Becton-Dickinson) followed by incubation with a fluorescein isothiocyanate-labeled goat anti-mouse secondary antibody. Finally, the nuclei are incubated with propidium iodide (PI) to label the DNA. Flow cytometric analysis is performed using two color analysis with emissions of fluorescein isothiocyanate detected with 530 nm short pass filters and PI detected with 630 nm long pass filters. In various embodiments, a minimum of 10,000 events is analyzed per sample, and the percentage of labeled cells is calculated.

As used herein, the second technique to measure the % IUdR-DNA cellular incorporation as a surrogate for IPdR-mediated tumor radiosensitization for "difficult to cure" human cancers involves the use of high performance liquid chromatography (HPLC). HPLC is a technique in analytic chemistry that is used to separate the components in a mixture, to identify each component, and to quantify each component. It relies on pumps to pass a pressurized liquid solvent containing the sample mixture (e.g. cellular DNA exposed to IUdR) through a column filled with a solid absorbent material. To measure the % IUdR-DNA cellular incorporation from tumor biopsies or circulating granulocytes taken from patients receiving po IPdR, single-cell suspensions are obtained similar to the processing for flow cytometry described above. Subsequently, single cells are disrupted and the DNA is enzymatically digested into free nucleosides. DNA extraction and digestion are performed by incubation with 10% trichloroacetic acid, followed by RNA digestion in 0.25M NaOH and enzymatic digestion with DNA-ase, alkaline phosphate and phosphodiesterase in MgCl and potassium phosphate buffer. A Waters 600E solvent delivery system on a 3.9×300 mm μ Bondapak reverse-phase column (Waters Corp, Milford, Mass.) is used. The mobile phase consists of 100 mm of sodium acetate buffer (pH 5.45) plus 7% (v/v) acetonitrile. Peak identification and quantitation of IUdR and thymidine (TdR) are performed against authentic nucleoside standards. The % IUdR-DNA replacement (or % TdR replacement) is calculated according to:

$$\frac{[mMoles\ IUdR] \times 100}{[mMoles\ IUdR + mMoles\ TdR]}$$

The therapeutic index (TI) of a drug is a quantitative relationship between the safety (toxicology) of a drug and its efficacy (pharmacology). A drug's TI is a ratio between two doses, the dose of the drug that causes adverse effects at an incidence/severity not compatible with the targeted indication divided by the dose that leads to the desired pharmacological effect. The actual TI (i.e. value), then, is wholly dependent upon the choice of doses used to calculate the ratio. Those choices are not standardized, as they necessarily vary depending upon the clinical situation. Historically, TI was determined in animals using the lethal dose of a drug for 50% of the population (LD50) divided by the minimum effective dose for 50% of the population (ED50), resulting in the TI=LD50/ED50; and in humans, safety was defined as the toxic dose in 50% of patients (TD50), and efficacy was defined as the efficacious dose in 50% of patients (ED50), and the TI for a drug was calculated as: TI=TD50/ED50. Even this definition still requires choices as to what is considered "toxic" and what is considered "efficacious." Modern pharmacology now qualifies the historical definition by recognizing that toxicity must be viewed in the context of the targeted indication (i.e. greater toxicity is acceptable if the indication is treating a lethal disease rather than a minor skin rash), and efficacy also must be defined for the specific circumstance (i.e. on the spectrum of any response to complete response). Even for a specific disease, the TI will vary depending upon the condition of the patients receiving the drug (e.g. older or debilitated patients will suffer more toxicities than healthy young patients). Because of the challenges inherent in making these choices for any given situation, TI is used as a concept rather than as an actual value. Drugs are broadly considered to have high or low TI's, and are compared on these relative scales. A high TI is obviously preferable, indicating that relatively little toxicity is seen at doses that achieve the desired response. Oncologic drugs, however, often have very low TI's (even <1, where toxicity is evident at subpharmacologic doses), and their use is justified by their indication, i.e. treating a lethal disease. Despite it's limitations, TI is a useful concept to consider when developing or evaluating a drug, because it has implications in terms of feasibility (i.e. can the drug be tolerated at a dose that effects any desired response) and applicability (i.e. is the drug so toxic that it's use is limited to lethal diseases or tolerated well enough to be appropriate for minor indications).

In preclinical (i.e. animal) studies of IPdR, no deaths were seen, even at very high doses (one dose/day×14-28 days), so the LD50 was never reached. Furthermore, these doses produced pharmacologic drug levels in the targeted tumor tissues (as measured by the % IUdR-DNA incorporation). Therefore, the TI of IPdR in animals was very high (technically, ∞ (infinity)) because the LD50 was never reached). The active drug, IUdR, is more toxic, but again, the LD50 was never reached in animal studies of IV IUdR. The mechanisms involved in the metabolism of IPdR have very favorable implications with respect to the TI of IPdR. IPdR must be converted to an the active drug IUdR, and this conversion occurs preferentially in liver and tumor cells compared to many other normal cells by virtue of the fact that many normal cells (specifically, bone marrow and gastrointestinal mucosal cells) do not possess the enzyme, aldehyde oxidase, to convert IPdR to the active drug. This profile, with minimal toxicity at pharmacologic doses makes IPdR an attractive drug for a variety of clinical indications. For example, IPdR may be added to regimens that are already being administered at their maximally tolerated dose (MTD) without the need to reduce doses of either IPdR or drugs within the regimen. Of utmost significance is the fact that the TI of IPdR predicts that it can be safely administered at pharmacologic doses in conjunction with radiation therapy (RT) delivered at different total RT doses and fractionation schedules.

The halogenated thymidine (TdR) analogs, bromodeoxyuridine (BUdR) and iododeoxyuridine (IUdR), are a class of pyrimidine analogs that have been recognized as potential radiosensitizing agents since the early 1960s. Their cellular uptake and metabolism are dependent on the TdR salvage pathway where they are initially phosphorylated to the monophosphate derivative by the rate-limiting enzyme, thymidine kinase (TK). After sequential phosphorylation to triphosphates, they are then used in DNA replication, in competition with deoxythymidine triphosphate (dTTP), by DNA polymerase. Indeed, DNA incorporation is a prerequisite for radiosensitization of human tumors by the halogenated TdR analogs, and the extent of radiosensitization correlates directly with the percentage TdR replacement in DNA (i.e. % IUdR-DNA incorporation). The molecular mechanisms of radiosensitization are most likely related to the increased susceptibility of TdR analog-substituted DNA to the generation of highly reactive uracil free radicals by ionizing radiation (IR), which may also damage unsubstituted complementary-strand DNA. Repair of IR damage may also be reduced by pre-IR exposure to these analogs.

Over the last 30 years, there has been renewed interest in these halogenated TdR analogs as experimental radiosensitizers in selected cancer patient groups. These analogs are rapidly metabolized in both rodents and humans, principally with cleavage of deoxyribose and subsequent dehalogenation by hepatic and extrahepatic metabolism, when given as a bolus infusion with a plasma half-life of <5 min. Consequently, prolonged continuous or repeated intermittent drug infusions over several weeks before and during irradiation are necessary, based on in vivo human tumor kinetics, to maximize the proportion of tumor cells that incorporate these analogs during the S phase of the cell cycle.

In the early 1980's, clinical testing of halogenated pyrimidines as radiosensitizers focused on patients presenting with high grade gliomas and sarcomas (Tables 1 and 2), although definitive phase III testing has not been performed. The magnitude of radiosensitization correlates directly with the % IUdR-DNA cellular replacement and determination of % IUdR-DNA cellular incorporation in tumor cells can serve as a predictive radiosensitization assay. Additionally, in small series of patients with head and neck cancers or liver metastases from colorectal cancer, the % IUdR-DNA cellular incorporation in tumors ranged from 5-8%, but was less than 1% in adjacent normal liver tissue, further supporting a therapeutic window for IUdR-mediated radiosensitization. Although IUdR has clear potential as a clinically active radiosensitizer, its development has been limited by the need for prolonged continuous infusion (ci), intra-arterial or intravenous, before and during RT to radiosensitize tumors. Prolonged ci of IUdR resulted in myelosuppression and acute GI toxicities, limiting the tolerated doses and the potential for clinical radiosensitization. Consequently, NCI or pharmaceutical companies did not pursue further clinical development of IUdR.

The pyrimidinone nucleosides, including 5-iodo-2-pyrimidinone-2'-deoxyribose (IPdR, were initially developed as antiviral agents, based on the hypothesis that nucleosides without an amino group or oxygen at position 4 would be substrates for viral but not mammalian TK. IPdR was found to have significant activity in herpes simplex virus-infected HeLa cells in vitro and in vivo following po administration without toxicity to uninfected cells or mice. IPdR has never been tested as an antiviral in humans. Although initial studies suggested that po IPdR did not require metabolism to IUdR for antiviral activity, subsequent studies demonstrated an aldehyde oxidase, which is present in both rat and mouse liver, that efficiently converts IPdR to IUdR. Saif et al., "IPdR: a novel oral radiosensitizer," Expert Opin Investig Drugs. 2007; 16(9):1415-24. Other normal tissues in the rat and athymic mouse including intestine, bone marrow, lung and kidney show 10-fold less activity of IPdR aldehyde oxidase. These findings led to a hypothesis that IPdR might increase the percentage IUdR-DNA incorporation and subsequent radiosensitization of actively proliferating primary or metastatic tumors in liver, while minimizing drug toxicity and/or radiosensitization to the adjacent quiescent normal liver parenchyma and possibly other rapidly proliferating normal tissues, including bone marrow and intestine. Dr. Cheng was issued a U.S. patent based on this hypothesis, entitled, "Determination of prodrugs metabolizable by the liver and the therapeutic use thereof" (U.S. Pat. No. 5,728,684) on Mar. 17, 1998.

In an initial publication regarding IPdR from Dr. Kinsella's laboratory, this hypothesis was tested using an athymic mouse model, in which a human colon cancer cell line (HCT-116), was established as a xenograft in subcutaneous (sc) flank tissue and as liver metastases using an intrasplenic implantation technique. IPdR was tolerated as a daily po bolus (via gastric gavage) for 6 days at a dose up to 1 g/kg/d, whereas po IUdR resulted in significant systemic toxicity (>10% body weight loss) at 250 mg/kg/d for 4 days. Pharmacokinetic analyses of po IPdR demonstrated efficient metabolism of IPdR to IUdR, with peak plasma levels of IUdR up to 45 µM within 15 min following bolus administration of 250 mg/kg IPdR. A 2-3 fold increase in the % IUdR-DNA cellular incorporation in tumor was found with IPdR at 1 g/kg/d for 6 days compared to the MTD of po IUdR (250 mg/kg/d for 4 days), but no differential effect of po IPdR on % IUdR-DNA incorporation was noted between liver tumor metastases and sc tumor. However, comparing the % IUdR-DNA cellular incorporation in two proliferating normal tissues (bone marrow and intestine), significantly less (≥2-fold) % IUdR-DNA incorporation was found with po IPdR than was found with po IUdR, whereas % IUdR-DNA incorporation was <1% in normal liver with either compound. Thus, initial in vivo results comparing % IUdR-DNA incorporation in tumors to proliferating normal tissues suggested that po IPdR has a potentially greater therapeutic index for IUdR-mediated radiosensitization of human tumors than does po IUdR.

In more recent pre-clinical studies using po IPdR, an improved therapeutic gain was documented for in vivo human tumor xenograft radiosensitization in athymic mice using daily po dosing of IPdR×6-14 days during RT compared to continuous intravenous (ci) infusion IUdR for similar time periods using maximum tolerated dose schedules of IUdR. The use of ci IUdR mimicked the route of administration used in the clinical trials of IUdR that demonstrated IUdR's potential for clinical radiosensitization (Tables 1 and 2). Using two different human colon cancer cell lines (HT-29 and HCT 116) and one human glioblastoma cell line (U251) as subcutaneous (sc) xenografts in athymic mice, we again found 2-fold increases in % IUdR-DNA tumor cell incorporation and 2-fold decreases in % IUdR-DNA cellular incorporation in proliferating dose-limiting normal tissues (bone marrow and intestine) following po IPdR compared to ci IUdR. Additionally, using a tumor regrowth assay to assess response to RT, we found a 1.3-6.0 fold sensitizer enhancement ratio (SER) (time to regrow to 300% initial tumor volume) with IPdR (qd×6-14 d) plus fractionated RT (2 Gy/d×4 d) in two human colorectal (HT-29 and HCT 116) and two glioblastoma xenografts (U251 and U87) compared to fractionated RT alone. Less (≤1.1) enhancement of the RT response was found using ci IUdR×6-14 d plus fractionated RT in these human tumor xenografts. Based on prior studies, the calculated SER for po IPdR of 1.3-1.5 would be predicted to result in clinically relevant radiosensitization of resistant human cancers.

To better explain this improved therapeutic index for human tumor radiosensitization using IPdR, we further investigated the pharmacokinetics of po IPdR using once daily dosings for 14 or 28 days in rodents. As demonstrated in our first po IPdR study, there was rapid and efficient conversion of IPdR to IUdR by a hepatic aldehyde oxidase in athymic mice. Plasma levels of IPdR and IUdR appeared to peak within 10-20 min of a po IPdR bolus. Plasma levels of IUdR decreased more rapidly than did IPdR over the first 90 min. Plasma levels of the other metabolites, IP and IU, reached a peak within 45-90 min following a po bolus of IPdR.

We also found that plasma levels of IPdR remain elevated at 45 and 90 min following po administration at the highest dose (1500 mg/kg). Although the persistent plasma levels of IPdR following 1500 mg/kg suggested a partial enzyme saturation of hepatic aldehyde oxidase, the prolonged IPdR plasma levels may also result from the fact that this highest dose required a slower bolus administration by gastric gavage over 15-20 min to reduce the risk of aspiration.

In another plasma PK study, we used once daily po IPdR dosing of 0.2 or 1.0 gm/kg/day (equivalent to 1200 or 6000 mg/m2)×28 days in Fischer-344 rats. This study was requested by the FDA as part of the pre-clinical testing of po IPdR prior to IND submission. Forty rats (10/sex/dosage group) were randomly assigned to the 2 dosage groups with multiple blood samplings on days 1 and 28, and single blood sampling prior to po IPdR on days 8 and 15. The IPdR and IUdR plasma concentration time profiles were evaluated using compartmental analysis modules and non-compartmental analysis, respectively. Absorption of po IPdR was not dependent on sex, dose, or single (Day 1) versus multiple daily dosings (Day 28). After single doses of 1.0 gm/kg/day, maximal concentrations of IPdR were achieved at 90 min after dosing. With increasing daily po dosing, Cmax values for IPdR were less than dose proportional and AUC values for IPdR after 28 days were less than those observed after Day 1. The mean elimination half-life for IPdR at the highest dose was ~5 hours. IUdR concentrations in these rats showed no sex differences, peaking by 15 min after dosing and AUC values were ~proportional with increasing dose. The mean half-life for IUdR was 6 and 8 hours for males and females, respectively. Thus, the PK profile for po IPdR appears quite similar in mice and rats.

Using cytosolic extracts from normal human liver specimens, we found that normal human liver has significant IPdR oxidase activity that results in a rapid (15 minute) conversion of IPdR to IUdR. The human liver IPdR-aldehyde oxidase was cytosolic, protein dependent, cofactor independent, and inhibited by low concentrations of menadione and isovanillin but not allopurinol. Menadione and isovanillin are selective inhibitors for aldehyde oxidase, and allopurinol is a selective inhibitor for xanthine oxidase. These results indicate that aldehyde oxidase but not xanthine oxidase is involved in the conversion of IPdR to IUdR in human liver. Moreover, the cytosolic localization and the lack of cofactors required for IPdR oxidase activity is consistent with aldehyde oxidase, which is a flavin adenine dinucleotide-containing enzyme that is oxidized by molecular oxygen but not by $\beta$-$NAD^+$ or other electron-transferring enzymes.

In contrast to human liver, we found that human small intestine had significantly lower log) IPdR oxidase activity that was not inhibited by isovanillin or allopurinol, but was stimulated by menadione. These results indicate that human intestine cytosol has some IPdR oxidase activity; however, this activity cannot be assigned to aldehyde oxidase or xanthine oxidase, and the importance of this activity and the enzyme system responsible for this activity remain to be determined. In addition, the activity of aldehyde oxidase in small intestine is considerably lower (>10-fold) than that found in liver when assayed with 6-methlypurine and would be expected to have less contribution to IPdR oxidase activity. We also confirmed that IPdR oxidase activity is not detectable in HT29 human tumor xenografts or in liver metastases obtained from two patients with colorectal cancer.

Orally administered IPdR appears to have limited systemic toxicities in rodents. Our first dose escalation study involved daily po bolus IPdR×6 days over the range of 500-2000 mg/kg/d. Using a change in the percentage body weight during treatment as an index of systemic toxicity, athymic nude mice tolerated the highest doses of IPdR (2000 mg/kg/d) with 10% body weight change. In comparison, athymic mice tolerated ci IUdR at 50 mg/kg/d for 6 days with 10-15% weight loss but experienced ≥20% weight loss by day 6 using 100 mg/kg/d.

In a second study, we evaluated the systemic toxicity of IPdR given as a daily po bolus for 14 days at either 750 or 1500 mg/kg/d in athymic mice. Using a change in the percentage body weight during drug treatment and for up to 28 days after treatment as an index of systemic toxicity, we found essentially no change in the percentage body weight gain for the 6 weeks of observation during and after drug treatment for the two IPdR groups compared to the control group receiving similar volumes of sterile water for 14 days by repeated daily oral gavage. Additionally, no other adverse effects were recorded regarding animal activity and behavior in the three groups of athymic mice (control, 750 or 1500 mg/kg/d) by daily observation. As such, we did not reach a MTD of IPdR using this 14-day daily po bolus schedule in athymic mice. No further dose escalations were used because of the increased risk of pulmonary aspiration with larger drug volumes (≥2000 mg/kg/d).

We used the Marshall Farms ferret (North Rose, N.Y.) as a non-rodent species for IPdR systemic toxicity and toxicology testing as required by the FDA. For this IPdR systemic toxicity and toxicology study, the twenty-four male or female ferrets were randomly assigned to four IPdR dosage groups receiving 0, 15, 150, and 1500 mg/kg/d by oral gavage×14 days prior to sacrifice on study day 15. No RT was administered to the ferrets. The dosage range and schedule of dosing were based on our prior pre-clinical studies of IPdR in athymic mice. All ferrets survived the 14-day treatment. Ferrets receiving 1500 mg/kg/d showed observable systemic toxicities with diarrhea, weight loss, and decreased motor activity beginning at days 5-8 of the 14-day schedule. Overall, both male and female ferrets receiving IPdR at 1500 mg/kg/d experienced significant weight loss (9% and 19%, respectively) compared to control following the 14-day treatment. No weight loss or other systemic toxicities were observed in other IPdR dosage groups. Grossly, no anatomic lesions were noted at complete necropsy, although liver weights were increased in both male and female ferrets in the two higher IPdR dosage groups. Histologically, IPdR-treated animals showed dose-dependent microscopic changes in liver consisting of minimal to moderate cytoplasmic vacuolation of hepatocytes which either occurred in the peri-portal area (1500 mg/kg/d dosage group) or diffusely throughout the liver (lower dosage groups). Female ferrets in the highest IPdR dosage group also showed decreased kidney and uterus weights at autopsy without any associated histological changes. No histological changes were found in CNS tissues. No significant abnormalities in blood cell counts, liver function tests, kidney function tests or urinalysis were noted following the 14-day treatment.

A second toxicology study of po IPdR used a once daily×28-day dosing schedule in male and female Fischer-344 rats. Again, no RT was administered. Eighty male and female rats (10/sex/dosage group) were randomly assigned to dosage groups to receive either 0, 0.2, 1.0 or 2.0 gm/kg/day×28 days and one-half were observed to day 57 (recovery group). Animals were monitored at least once daily and weighed every 3-4 days during the IPdR dosing period and then weekly to day 57. Blood testing, including a CBC with differential and a comprehensive chemistry panel, was performed on Days 0, 8, 15, 29, 43 and 57. Five male and five female rats from each dosage group underwent full necropsy on either Day 29 or 57 of the study. Rodent housing and feeding guidelines were similar to our prior toxicology study in ferrets.

IPdR-related effects were clinically evident at 1.0 and 2.0 gm/kg/day groups as indicated by observation of hunched posture, rough coat or thin appearance. The 2.0 gm/kg/day males experienced significant decreases in mean body weights (8-11%) beginning on day 5 and continuing through the 28 day treatment period; but the weight loss was readily reversible once treatment was completed. No drug-related deaths occurred and only one animal (male, 2.0 mg/kg/day group) had a gross pathology finding, a small thymus gland with microscopic evidence of thymic lymphoid depletion.

Importantly, no severe histopathologic changes were found at the interim (Day 29) or final (Day 57) necropsies in any tissue/organ.

A first-in-human Phase 0 non-therapeutic trial of oral IPdR in patients with advanced malignancies was published in 2013 from the Center for Cancer Research, NCI. The objective was to determine whether the oral route of administration of IPdR was a feasible alternative to continuous intravenous infusion of IUdR, as suggested from our preclinical studies cited above. A single po dose of IPdR was administered, and patients were followed for 14 days for safety assessments. Dose escalations were planned (150, 300, 1200, and 2400 mg) with one patient per dose level and 6 patients at the highest dose level. The starting dose of 150 mg was based on 10% of the tolerable dose from a repeat-dose study in the most sensitive animal species, the ferret, as described above. Blood sampling was conducted over a 24-hour period for pharmacokinetic analysis.

A total of 10 patients participated in the study and all patients tolerated the IPdR well with no drug-related adverse events, according to NCI Common Toxicity Criteria version 4.0. Plasma concentrations of the active metabolite, IUdR, generally increased as oral doses of IPdR escalated from 150 mg to 2400 mg. At the highest IPdR dose of 2400 mg, all 6 patients achieved peak IUdR plasma levels of 4.0+/−1.02 umol/L after 1.67+/−1.21 hours and IUdR plasma levels remained above 1 umol/L for 3-4 hours with a half-life of 1.5 hours.

This trial showed the ability of a small Phase 0 study to provide critical information for decision making regarding future development of a novel radiosensitizing drug like IPdR. Adequate plasma levels of IUdR were obtained to justify proceeding with further clinical development of oral IPdR in combination with radiation, as described by this invention.

Based on these extensive pre-clinical studies (summarized in Table 3) that led to the FDA IND, four conclusions were reached by the inventor that served as guidelines for the design of the ongoing Phase I and Pharmacokinetic clinical trials of IPdR+RT. First, orally administered IPdR has been demonstrated to be an effective in vivo radiosensitizer using four different human tumor xenografts (two colorectal cancer and two glioblastoma cell lines) in athymic mice. Compared to either po or ci IUdR, a 2-fold increase in % IUdR-DNA tumor cell incorporation and a 2-fold decrease in % IUdR-DNA incorporation in proliferating dose-limiting normal tissues (bone marrow and intestine) is found following po IPdR×6-14 days. Greater tumor radiosensitization, using a regrowth delay assay of these human tumor xenografts in athymic mice, was also found with po IPdR (sensitizer enhancement ratios of 1.3-6.0) versus continuous infusion IUdR (sensitizer enhancement ratio of 1.1). Thus, po IPdR has a greater therapeutic index (TI) for IUdR-mediated radiosensitization in human tumor xenografts in athymic mice compared to the parent compound, IUdR. We did not establish a MTD in athymic mice for IPdR over the dose range used.

Second, in contrast to our studies in athymic mice in which no significant systemic toxicities were found with daily po IPdR doses of 1500 mg/kg/d×6-14 days, we found significant weight loss (10-20% body weight) and gastrointestinal side effects in ferrets receiving 1500 mg/kg/d×14 days and significant weight loss (~10%) in male rats receiving 2 gm/kg/day×28 days. Mild to moderate microscopic histopathologic changes were noted in hepatocytes in an IPdR dose-dependent manner in ferrets and rats. No other gross or microscopic changes were noted at complete necropsy. Additionally, no changes in blood counts, liver function tests, renal function tests or urinalysis were found. While no toxic deaths were found in the ferret or rat studies, we assigned the MTD for po IPdR at 1500 mg/kg/d×14 days and <2000 mg/kg/d×28 days.

Third, based on our pharmacokinetic data in Rhesus monkeys, rats, and in athymic mice, we conclude that oral or iv IPdR is rapidly cleared from plasma in a bi-exponential fashion. However, it is also evident that IPdR oxidase activity is partially saturable following high (>1000 mg/kg) single doses in mice and following repeated daily doses over two weeks in ferrets and over four weeks in rats. Collectively, these rodent and mammalian data of IPdR indicate the need for a careful, human pharmacokinetic study of po IPdR as part of the initial Phase I clinical trials. We have already determined that normal human liver has significant IPdR-aldehyde oxidase activity. Human liver IPdR-aldehyde oxidase is cytosolic, protein dependent, and co-factor independent. It is inhibited by low concentrations of menadione and isovanillin, but not allopurinol. Menadione and isovanillin are selective inhibitors for aldehyde oxidase while allopurinol is a selective inhibitor for xanthine oxidase. Thus, our pre-clinical results indicate that a human hepatic aldehyde oxidase, but not a hepatic xanthine oxidase, is involved in the conversion of IPdR to IUdR. It has been previously reported that kinetically distinct forms of aldehyde oxidase exist in male and female rodent liver, and that these distinct forms occur as a result of differences in redox state and not in cDNA sequencing. However, a gender difference in enzyme activity, as defined by in vitro conversion of IPdR to IUdR, was not evident in our studies in ferrets or athymic mice. A high degree of homology exists between mouse and human aldehyde oxidase.

Fourth, based on the systemic toxicity data, the FDA recommended a starting po IPdR dose of 85 mg/m$^2$ (150 mg) qd×28 days (≅0.1 MTD) in humans for the initial Phase I trials. The 28-day, once daily schedule was chosen to provide adequate drug exposure prior to (one week) and during (three weeks) RT to affect radiosensitization. Based on the observed gastrointestinal toxicity seen in the ferret study and the higher % IUdR-DNA levels in normal intestine cells compared to normal bone marrow cells found in our previously published IPdR studies in athymic mice, we are carefully monitoring patients for gastrointestinal toxicity using the NCI Common Toxicity Criteria, version 4.0. Again, we have already determined that human small intestine has significantly lower IPdR oxidase activity (≥10-fold reduction) compared to normal human liver. If IPdR can be safely administered in humans with favorable pharmacokinetics and increased % IUdR-DNA cellular incorporation in tumors compared to dose-limiting proliferating normal tissues, it should greatly reduce the cost and complexity of administration of a halogenated thymidine analog for human tumor radiosensitization compared to prolonged continuous intravenous or intra-arterial infusions as required for the parent compound, IUdR.

Many of the commonly used chemotherapeutic drugs, as well as RT, target DNA for cytotoxicity. Indeed, the subsequent DNA damage response to these cancer treatments in both malignant and normal tissues determines the therapeutic index (TI). The DNA damage response is a complex process involving multiple DNA repair, cell survival, and cell death pathways with both damage specificity and coordination of the DNA damage response to different types of DNA damage. These DNA damages include double-strand breaks (DSB), single strand breaks (SSB), base damages, bulky adducts, intra/interstrand cross links, and breakdown of replication fork lesions.

The cytotoxic response to combining IPdR+RT is mediated through the DNA damage response in both malignant and normal tissues. It is also now understood that human cancers typically arise after a long process of random gene mutations, particularly arising during repeated cell divisions of normal self-renewing ("stem") cells that maintain normal tissue homeostasis. Some of these mutations that lead to cancer involve genetic changes in key DNA repair pathways, including both DNA mismatch repair (MMR) and base excision repair (BER). Additionally, epigenetic changes via DNA methylation and acetylation at DNA repair genes can lead to cancer. As such, cancer treatments that target a specific DNA repair defect can be selectively toxic (i.e. lethal) to cancer cells with different DNA repair capacities while sparing normal (DNA repair proficient) cells. Based on pre-clinical cellular and molecular studies by Dr. Kinsella's laboratory, it is known that specific IUdR-DNA mismatches (particularly G:IU mismatches) are recognized and repaired efficiently by both MMR and BER in normal cells. However, MMR-deficient (MMR$^-$) and/or BER-deficient (BER$^-$) cancers do not recognize nor repair the G:IU DNA adducts caused by IUdR or IPdR treatment, resulting in increased IUdR-DNA incorporation and enhanced IR cytotoxicity. Consequently, targeted treatment using IR+IPdR of MMR$^-$ and/or BER$^-$ human cancers will be exploited by this invention.

MMR is a highly conserved, but complex, DNA repair system that helps maintain genomic stability in human cells on several levels, including correcting base-base mismatches and insertion-deletion loops (IDLs) erroneously generated during DNA replication. MMR also mediates cell cycle and cell death in response to certain types of endogenous DNA damage and exogenous DNA damage from occupational and therapeutic chemical and ionizing radiation exposures. As such, MMR plays an essential role in the overall DNA damage response in humans by removing severely damaged cells and reducing the risk of mutagenesis and carcinogenesis. However, in the absence of MMR (i.e. MMR deficiency; MMR$^-$), resulting from genetic and/or epigenetic alterations in the human MMR genes, the persistent DNA base-base mismatches and IDLs remaining after DNA replication result in a mutator phenotype with a $10^2$-$10^3$ elevation of spontaneous mutations highlighted by microsatellite instability (MSI) and a significant risk of cancer.

MMR deficiency is principally associated with the autosomal dominant Lynch Syndrome, a consequence of mutations in MMR genes. MMR deficiency is also associated with an increasing number of sporadic (non-genetic) common solid cancers, typically related to promoter methylation of the hMLH1 and hMSH2 genes. These sporadic MMR deficient human cancers include several types of gastrointestinal cancers (colorectal, pancreatic, gastric, esophageal), gynecologic cancers (endometrial, ovarian), genitourinary cancers (bladder, ureter), as well as non-small cell lung cancers (NSCLC) and primary adult brain tumors, where MMR deficiency (detected by standard pathological immunohistochemistry (IHC) testing of MMR protein levels in these tumors is found in up to 5-15% or more of these common cancers.

In pre-clinical (laboratory based in vitro/in vivo) studies of MMR-deficient human cancer cells, resistance ("damage tolerance") is found to multiple different classes of clinically active chemotherapy drugs, including temozolomide, topotecan, cisplatinum, carboplatinum, 5-fluorouracil (5-FU), and 6-thioguanine (6-TG), as well as to ionizing radiation. The clinical implications for the treatment of MMR-deficient sporadic human cancers are of both prognostic and predictive significance. For example, promoter hypermethylation of hMLH1 or hMSH2 with subsequent loss of protein expression of these key MMR regulation proteins by IHC testing is found in nearly 50% of NSCLCs occurring in non-smokers, and is associated with a poor prognosis, even in early stage disease. Additionally, recent analyses of multiple clinical trials of the use of 5-FU (±concomitant cisplatinum or oxaloplatinum) as adjuvant treatment in MMR-deficient colon and esophageal cancers found significantly less benefit in disease-free and overall survival in comparison to a significant benefit in MMR-proficient colon and esophageal cancers, respectively. MMR-deficient endometrial and rectal cancers also show reduced local control and lower pathological response rates following RT alone or with combined 5-FU and RT. Finally, MMR-deficient malignant gliomas (high grade adult brain tumors) were noted to have a markedly reduced response rate and survival time compared to MMR-proficient gliomas when treated with concomitant RT and temozolomide.

MMR deficiency occurring during or following cancer treatment, related to MMR gene mutations or methylation/acetylation of the gene promoter, may also be associated with a poor prognosis. Somatic point mutations in MSH6 are found in up to 30% of recurrent/progressive glioblastomas, which were not present in pre-treatment specimens. Indeed, inactivation of MSH6 was correlated with prior or ongoing temozolomide exposure and associated with enhanced tumor regrowth and shorter survival. Decreased protein expression of MLH1 following doxorubicin-based chemotherapy in breast cancer patients was also reported to correlate significantly with a reduced disease-free survival (p=0.0025). Finally, promoter methylation of MLH1 in plasma DNA after cisplatin-based chemotherapy for ovarian cancer predicted a poor survival.

Thus, these clinical data underscore the observed resistance ("damage tolerance") to different classes of chemotherapy drugs alone, radiation therapy alone, and chemotherapy-radiation therapy combined treatments found in the pre-clinical studies in MMR-deficient vs MMR-proficient human cancer cells as mentioned above. This invention, IPdR+RT, is designed to overcome the "damage tolerance" of MMR-deficient cancers and will be used clinically in different types of MMR-deficient cancers.

BER is the major DNA repair pathway involved in the removal of nonbulky base damages induced by endogenous and exogenous adducts. A major source of endogenous base damage involves oxidative base modifications from reactive oxygen and nitrogen species during normal cellular respiration or during oxidative stress from ischemia or chronic inflammation. BER is also the major repair pathway for nonbulky damaged bases, abasic sites, and DNA SSBs after treatment with ionizing radiation, monofunctional alkylating drugs (e.g. temozolomide), and certain antimetabolites including the thiopurines (e.g. 6-thioguanine (6-TG) and 6-mercaptopurine (6-MP)), the fluoropyrimidines (e.g. 5-FU), and the halogenated thymidine analogues, IUdR and its prodrug, IPdR. Thus, BER and MMR pathways are activated by similar types of DNA damage-targeted cancer treatments and are involved in damage (sub) processing of both IUdR and IR as pertains to this invention, as well as other chemotherapeutic drugs (e.g. 6-thioguanine, 6-TG).

BER is a complex multistep pathway initiated by damage-specific DNA glycosylases, which create abasic or apurinic/ apyrimidinic (AP) sites by cleaving the N-glycosidic bond and holding the base onto the sugar-phosphate backbone. Next, AP endonuclease 1 (APE 1) recognizes the AP sites and cleaves the DNA phosphodiester backbone leaving a 3'-hydroxyl group and a 5'-deoxyribose phosphate group flanking the nucleotide gap. Subsequent repair proceeds by two subpathways, both initiated by DNA polymerase β, for 1 nucleotide repair (short-patch BER) or for 2 to 15 nucleotides repair (long-patch BER). Although these two subpathways use different subsets of enzymes, there is cooperation and compensation between the short-patch and long-patch pathways. It is generally held that short-patch BER accounts for most BER activity after chemotherapeutic treatment and/or RT.

BER processing typically leads to chemotherapy drug and IR resistance. Consequently, the recognition and detection of BER-deficient cancers and/or the development of chemical inhibitors of specific BER enzymes can reverse alkylating and anti-metabolite drug resistance, as well as IR resistance. Based in part on the pre-clinical results from Dr. Kinsella's lab, methoxyamine (MX), a chemical inhibitor of BER, is currently undergoing clinical testing as TRC-102 in combination with chemotherapy drugs including temozolomide. MX is a small organic amine derivative of alkoxyamine that blocks the short patch BER pathway by covalently binding the AP site formed by a specific glycosylase, rendering it refractory to the catalytic activity of AP endonuclease 1. A MX-bound AP site is repaired much more slowly (>300×) than a normal AP site, and enhances cell death. The Kinsella lab has also demonstrated that the combination of IUdR+MX enhances % IUdR-DNA incorporation and radiosensitization in several experimental human cancer cell models.

Targeting the clinical use of IPdR as a radiosensitizing drug for MMR-deficient (damage tolerant) human cancers as part of this invention will also be extended to targeting BER deficiency in these damage-tolerant cancers with the use of methoxyamine (MX) or other chemical APE1 inhibitors currently undergoing clinical development. The highlights of this targeted approach are as follows. First, from a molecular biochemical perspective, specific IUdR-DNA mismatches (i.e., G:IU but not A:IU) are recognized and efficiently repaired by MMR. Consequently, MMR-deficient tumors retain significantly higher IUdR-DNA levels compared with proliferating MMR-proficient normal tissues. Because the level of IUdR-DNA incorporation directly correlates with the extent of tumor radiosensitization, MMR-deficient human cancers can be selectively targeted to increase ionizing radiation cytotoxicity. Additionally, use of a chemical inhibitor of BER, such as methoxyamine (MX), will increase the % IUdR-DNA tumor cell incorporation, as the G:IU mismatch can also be processed (removed) by BER. This chemical inhibition of BER will further increase the % IUdR-DNA tumor cell incorporation and subsequent IUdR-mediated radiosensitization. Finally, BER-deficient cancers will be directly targeted by IPdR+RT as part of this invention.

Second, using a probabilistic model of the cell cycle, faster cell cycling in MMR-deficient versus MMR-proficient cells is noted by the inventor, and from this, a computational model can predict when tumor cells with higher IUdR-DNA levels should be irradiated as tumor cells accumulate in more ionizing radiation-sensitive cell cycle phases.

Third, the therapeutic index for this treatment strategy can be assessed by quantifying IUdR-DNA incorporation levels in biopsy specimens of MMR-deficient or BER-deficient tumors versus dose-limiting MMR-proficient and BER-proficient normal tissues (e.g. circulating granulocytes) by routine immunohistochemistry and flow cytometry with anti-IUdR antibodies and/or by high performance liquid chromatography (HPLC) approaches. Details of these techniques are previously provided under DEFINITIONS. Indeed, a proof-of-principle human tumor xenograft study in athymic mice was performed by Dr. Kinsella's lab, and showed persistently higher IUdR-DNA incorporation in MMR-deficient vs MMR-proficient tumor and a 40% prolongation of tumor response with no dose limiting systemic toxicities.

Extensive preclinical data and limited clinical (Phase I and Phase I/II) studies (summarized in Tables 1 and 2) have demonstrated the radiosensitizing effect of ci IUdR in clinically radioresistant cancers such as high-grade gliomas and soft tissue sarcomas. These studies have also demonstrated that IUdR is incorporated into DNA; this incorporation can be reliably measured; and that the % IUdR-DNA cellular incorporation is directly and linearly related to the plasma level of IUdR (plasma level of >1 µmol/L to achieve >3% IUdR-DNA cellular incorporation). Despite these positive findings, further development of IUdR as a clinical radiosensitizer has not been pursued because the dose of IUdR that is required to achieve plasma levels adequate for radiosensitization (i.e. >1 µmol/L to achieve >3% IUdR-DNA cellular incorporation) cause unacceptable normal tissues toxicity, and are thus not tolerable (i.e. IUdR has an unacceptable therapeutic index). In addition, the required mode of administration of IUdR, namely continuous intravenous administration throughout an entire course of radiation of up to 6 weeks, makes IUdR technically untenable to deliver in a reasonable clinical setting. So, the addition of IUdR to the combined modality (i.e. RT+chemotherapy) approaches that now serve as the standard of care for the treatment of many cancers has not been studied.

In contrast, IPdR, a prodrug of the radiosensitizer IUdR, is a novel orally available nucleoside analog that is predictably and efficiently absorbed in the GI tract and metabolized in the liver by aldehyde oxidase to IUdR. In addition to the advantage of ease of administration, the metabolism of IPdR to IUdR in vivo results in two additional major advantages of po IPdR compared to ci IUdR. First, compared to ci IUdR, oral IPdR generates 2-3 fold increased % IUdR-DNA incorporation into tumor tissues, and second, oral IPdR results in a 2-3 fold decreased % IUdR-DNA incorporation into proliferating normal tissues (bone marrow and intestine) as a consequence of the properties and biodistribution of aldehyde oxidase, the enzyme that converts IPdR to IUdR. Thus, as opposed to ci IUdR, po IPdR can be delivered at a dose that is both tolerable and that produces plasma levels of IUdR adequate for effective radiosensitization.

Adding po IPdR to RT or combined RT+chemotherapy treatment regimens, then, can be expected to be feasible, tolerable, and moreover, improve the overall efficacy of these treatments for several solid adult cancers. The clinical use of IPdR+RT to target sporadic MMR-deficient and/or BER-deficient cancers is already discussed above. Additionally, IPdR may be particularly valuable as a component of the following combined modality regimens: for high-grade brain tumors, (IPdR+RT)±temozolamide (TMZ); for rectal and gastric cancers, (IPdR+RT)+fluoropyrimidines (e.g. 5-fluorouracil (5-FU), capecitabine); and for head&neck and cervical cancers, (IPdR+RT)+platinum analogs (e.g. cisplatin (CDDP)); and for pancreatic, gynecologic and head & neck cancers, (IPdR+RT)+ribonucleotide reductase inhibitors.

A brief description of IPdR+RT+chemotherapy combinations for clinical use include the following.

First, Improvement in the TI of RT+/−TMZ in high-grade brain tumors. High-grade brain tumors, including anaplastic astrocytomas (AA) (Grade 3 of 4) and glioblastoma multiforme (GBM) (Grade 4 of 4) are highly malignant tumors, currently not curable. Approximately 13,000 patients are diagnosed with these diseases yearly in the U.S. These tumors rarely metastasize outside of the brain, and typically recur locally following initial surgery (maximum safe resection) followed by concomitant RT+TMZ, and later, adjuvant TMZ. The median survival for these tumors is ≈3.4 years for AA and 14-18 months for GBM. The clinical data for the prior clinical trials of RT+ci IUdR (from the 1980-1990's, prior to the present use of RT+TMZ) are previously reviewed in Table 1, and are similar to the median survival for the current use of RT+TMZ. Pre-clinical data on RT+po IPdR using two different human glioblastoma xenografts suggest further improvement in the therapeutic index (TI).

As currently used, TMZ is the most effective chemotherapy drug for patients with high risk low grade glioma and high-grade gliomas, and is routinely used on a daily basis during a typical 6-week course of post-operative RT, based on clinical Phase 2 and 3 trials. However, the biochemical and molecular interactions of TMZ+RT are only additive, not synergistic as is the IPdR+RT interaction as described in detail herein.

Over the last decade, the molecular analysis of high-grade gliomas has principally focused on defining the methylation status of the promoter region of MGMT as a prognostic marker of survival and as a predictive assay of TMZ efficacy on the tumor. MGMT promoter methylation is found in approximately 40% of high-grade gliomas in adults and 80% in the much less common pediatric high-grade gliomas. In clinical trials of RT+TMZ in adult GBM patients, RT+TMZ was more effective (5-month survival benefit to 15 months, similar to the prior RT+ci IUdR data as presented in Table 1) compared to RT alone in patients whose tumors showed methylated MGMT. No survival advantage was found using RT+TMZ compared to RT alone in unmethylated MGMT GBM patients, representing 60% of all GBM patients. However, despite MGMT methylation status-directed therapy for adding TMZ to RT, virtually all patients with high-grade gliomas will progress locally in brain, and succumb to the disease. As such, newer (more novel) RT treatment options are sorely needed for high-grade gliomas.

Dysregulation of other DNA repair pathways, including both MMR and BER, are reported to contribute to the aggressive biology and poor prognosis of high-grade gliomas. In a recent comprehensive analysis of the messenger ribonucleic acid (mRNA) expression levels in 157 DNA repair genes in two large, publically available, gene expression data sets from 699 GBM tumors, the expression levels of a key BER glycolylase (APE1) and a key MMR protein (PMS2) were reported to be independent prognostic biomarkers of survival following treatment with RT alone or TMZ alone. Based on this novel DNA repair prognostic index for GBM and other high-grade gliomas, future clinical studies of the use of RT+IPdR would stratify for specific molecular subsets of high-grade gliomas with intact MGMT (i.e. unmethylated promoter) and deficient MMR. Alternatively, combinations of RT+IPdR+TMZ would be recommended for high-grade gliomas with methylation of the MGMT promoter and low APE1 expression, representing deficient BER. In both clinical scenarios, the enhanced IPdR-mediated radiosensitization would be predicted to improve the duration of survival by 50%, as reflected in the early trials of ci IUdR+RT (Table 1).

Second, improvement in the TI of RT+fluoropyridimine (FP)-based chemotherapy as pre-operative adjuvant treatment in locally advanced rectal cancers. Adjuvant therapy for solid tumors, including locally advanced rectal cancer (≈10,000 cases/yr in the U.S.), is designed to cure patients more often than surgery alone. The first principles of curative adjuvant therapy are to improve both local tumor control and reduce the development of systemic (metastatic) disease. Through the mid-1980's, locally advanced rectal cancer, defined by tumor extension through the rectal wall (called $cT_3$ or $T_4$ disease) or involvement of locoregional pelvic lymph nodes (called $N_1$ or $N_2$ disease) was treated surgically with a cure rate of only 35-40% and a high risk of local recurrence (25-35%) and developing metastatic disease. Over the last three decades, pre-operative RT+concomitant FP-based chemotherapy (initial continuous intravenous 5-FU and now twice daily po capecitabine) followed by total mesorectal excision (TME) surgery has improved the overall cure rate up to 65-70% in this patient group.

It is now recognized that the pathologic tumor response to locally advanced rectal cancer following RT+FP-based chemotherapy is of prognostic significance for predicting local control, disease-free survival (DFS) and overall survival (OS) with ten years of follow-up. In the 10-15% of patients whose resected tumors following pre-operative RT+FP treatment showed no residual viable tumor cells (i.e. a complete pathologic response (pCR)), 10-year DFS approached 90%. In contrast, the vast majority of similarly treated locally advanced rectal cancer patients whose resected tumors showed intermediate tumor regression (65% of patients) or poor tumor regression (25-30% of patients) achieved lower 10-year DFS, 70% and 60%, respectively. Thus, the pCR rate following pre-operative RT+FP treatment is a valid intermediate for this patient group based on this study and others.

More recently, clinical trials for locally advanced rectal cancer patients have attempted to improve the pCR rate by adding other cytotoxic chemotherapy drugs (e.g. oxaliplatin) or biologic agents (e.g. cetuximab, an epidermal growth factor inhibitor) during pre-operative RT+FP without any improvement in pCR rate, but with increased normal tissue complications, representing a decrease in the therapeutic index (TI).

The biochemical and cellular interactions of RT+FP are felt to result from inhibition of the enzyme, thymidylate synthetase (TS) by the FP monophosphate metabolite, FdUMP, leading to decreased (or unbalanced) nucleotide pools necessary for DNA synthesis and decreased DNA repair following RT damage. Intracellular IPdR monophosphate metabolite, IdUMP can inhibit (by binding) TS leading to increased FP-mediated radiosensitization as well as enhancing IPdR-mediated radiosensitization secondary to IUdR-DNA incorporation. Consequently, the use of po IPdR added to the current standard-of-care pre-operative adjuvant therapy (i.e. RT+twice daily po capecitabine) is postulated to increase the pCR rate from 10-15% to 30-35% based on the IPdR+FP interactions and IPdR+IR interactions found experimentally in human colorectal cancer cells. Such an increase in the pCR rate should translate into a further 10-15% improvement in DFS for patients with locally advanced rectal cancer. The concept of testing this hypothesis in a Phase II clinical trial of po IPdR+RT+twice daily po capecitabine was favorably reviewed when presented in November 2014 to the NCI Rectal Cancer Radiotherapy Working Group. Currently, a NCI-sponsored initial Phase I and PK clinical trial of po IPdR+RT for patients with metastatic gastrointestinal cancers, including rectal cancer (NCI Protocol #9882; http://www.cancer.gov/about-cancer/treatment/clinical-trials/search/results?protocol-searchid=14235539), with Dr. Kinsella as the Principal Investigator, is ongoing. The clinical and PK data from this ongoing clinical trial will be used in the design of a future Phase II clinical trial of IPdR+RT+twice daily po capecitabine as pre-operative therapy in patients with locally advanced rectal cancer.

Third, improvement in the TI of RT+platinum (PA) compounds in head and neck cancers and cervix cancer. Platinum-based (PA) compounds form a distinct class of cytotoxic chemotherapy drugs characterized by their unique metallic element. The initial PA drug, cis-platin (cis-diamminedichloroplatinum II) exerts its cytotoxicity by inhibiting DNA synthesis, as well as by inhibition of transcription elongation by creating DNA intrastrand crosslinks. In vitro experiments in rodent and human cancer cells suggest greater than additive interactions of PA with IR, mediated by inhibition of DNA repair. A unique in vitro biochemical interaction of cisplatin and IUdR previously reported results in increased DNA crosslinks and enhanced cytotoxicity in a human bladder cancer cell line. Specifically, the effect of increasing concentrations of IUdR for 48 hours prior to a one-hour exposure to cisplatin demonstrates dose-modifying factors of up to 3.5 at 10% survival. In addition, a time course for formation of an IUdR-platinum (Pt) adduct is compared to a deoxyguanine (dGua)-platinum (Pt) adduct that appears slower, but is similar to that of a deoxycytidine-platinum adduct. Two specific chemical structures of the IUdR-Pt adducts are proposed. Thus, these experimental data suggest that the proposed clinical use of RT+po IPdR with daily to weekly PA treatment would be expected to enhance the efficacy of PA adduct formation (and tumor cytotoxicity) and further enhance the well-established effect of RT in these common tumor sites in a greater than additive (i.e. synergistic) manner. Importantly, it is hypothesized that there would be no overlap of the known dose-limiting systemic normal tissue toxicities of PAs, that include myelosuppression, renal toxicity, ototoxicity and peripheral neuropathy with the concomitant use of po IPdR, based on the pre-clinical IPdR toxicology data. Clinically, the combination of RT+PA-based chemotherapy (typically, cis-platinum) has been demonstrated to be more effective than RT alone for patients with locally advanced squamous cell carcinomas (SCC) arising from the head and neck (H&N; ≈15,000 cases/year in the U.S.), as well as to the cervix (≈12,000 cases/year in the U.S.), based on multiple randomized clinical trials over the last 2+ decades. As such, RT+PA remains the standard-of-care for both disease sites, and future clinical trials to further improve the cure rate for these two patient groups will incorporate IPdR into these RT+PA regimens.

As a proof of principle for future use of po IPdR combined with RT+PA chemotherapy, the threshold of % IUdR-DNA tumor cell incorporation (≥3%) associated with in vivo radiosensitization has already been confirmed in prior clinical Phase I trials of ci IUdR (or BUdR)+RT for both patients with locally advanced H&N SCC and cervical SCC. Using ci IUdR at 1000 mg/M$^2$, a dose that produces plasma levels of IUdR-DNA tumor cell levels plateaued at 7.5-8% within 5 days, suggesting a 1.3% DNA-replacement/day in H&N SCC. A similar dosing of ci BUdR (1000 mg/M$^2$/day×4 days, repeated weekly for 6 weeks) in patients with locally advanced cervical cancer resulted in tumor cell IUdR-DNA incorporation of 5-8% on Day 5 following a 4-day ci treatment. Furthermore, this level of IUdR incorporation into tumor cells compared favorably to the 3-4% IUdR-DNA incorporation in adjacent normal rectal mucosa cells, demonstrating a 1.5-1.8-fold ratio of tumor to rectum. By extrapolating to the pre-clinical and clinical Phase 0 trials of po IPdR, the higher transient plasma levels of IUdR (up to 4 μMol/L), as well as the favorable tumor-normal tissue (bone marrow; bowel epithelium) % IUdR-DNA cellular incorporation ratios from the mouse human tumor xenograft studies as previously described, should result in an improved TI for the use of po IPdR with RT+PA in locally advanced cervix cancer patients.

Fourth, improvement in the TI of RT+ribonucleotide reductase (RR) inhibiting chemotherapy drugs in pancreatic, gynecologic and head & neck cancers. RR inhibiting chemotherapy drugs, including hydroxyurea, gemcitabine, fludarabine, motexafin gadolinium and 3-aminopyridine-2-carboxaldehyde thiosemicarbazone (3AP, triapine) have been studied as potential radiosensitizing drugs for over three decades in both the laboratory and clinic. RR is the rate limiting enzyme in the synthesis and repair of DNA and is the only enzyme responsible for the conversion of ribonucleotide diphosphates to deoxyribonucleotide diphosphates, the fundamental building blocks of DNA synthesis and repair. RR is a heterodimeric tetramer comprised of two dimers. R1 (also called RR M1) is the large regulatory subunit that is constitutively expressed through the cell cycle and can bind the nucleoside analogs gemcitabine and fludarabine. There are two smaller subunits called R2 (or RR M2) and a p53 inducible homolog of the R2 subunit (known as p53R2) that can bind to the R1 dimer to form the active enzyme.

There are two major theories involving the role of RR in processing ionizing radiation (IR) damage. The first, derived from experimental data, is that the R2 protein is unregulated following IR providing more (sufficient) deoxyribonucleotide triphosphates (dNTPs) for DNA repair of IR-induced damage. The second theory involves upregulation of p53R2 protein, again to result in increased dNTP pools for IR-induced damage repair. It has also been found that the use of non-cytotoxic doses of the RR inhibitor hydroxyurea and clinically achievable levels of IUdR (2 μM) resulted in a 2-fold increase in IdUTP pools and IUdR-DNA incorporation resulting in a greater that additive (approximately 1.75) radiation sensitizer enhancement killing of human bladder and cervical cancer cells in vitro.

Clinically, these RR inhibitor chemotherapy drugs, particularly hydroxyurea, gemcitabine and triapine have been administered during RT with an improvement in the TI for locally advanced cervix, head & neck and pancreas cancers based on clinical Phase 2 and 3 trials. Additionally, the dose limiting toxicity with these RR inhibitors is principally myelosuppression, and in the preclinical IPdR toxicity studies, significant myelosuppression was not encountered, so the addition of IPdR to RR inhibitor therapies should be feasible and tolerable. Local tumor control with RR inhibitors+RT is improved over RT alone by only 10-30%. It is postulated that the addition of IPdR could further improve local control as well as overall cure rates, particularly in cervix and head & neck cancers. Indeed, it is already demonstrated in a small clinical trial that ci IUdR+RT results in a high local control rate of locally advanced head & neck cancers with % IUdR-DNA levels >5% following a 5-7 day ci IUdR infusion.

As part of this invention, an assay will be further developed clinically to predict the extent of IUdR-mediated radiosensitization by IPdR, as well as tumor proliferation before and during RT, and the potential normal tissue toxicities from IPdR±RT in selected cancers as previously described. The percentage IUdR-DNA incorporation in a tumor cell (in vitro) or tissue (in vivo) correlates directly with the extent of radiosensitization. Pre-clinical in vivo testing of oral IPdR as a prodrug for IUdR-mediated radiosensitization, consistently found 2-fold increases in the percentage IUdR-DNA tumor cell incorporation and 2-fold decreases in percentage IUdR-DNA incorporation in proliferating dose-limiting normal tissues (bone marrow and intestine) following oral IPdR compared to ci IUdR (using MTD schedules) in four different human tumor xenografts in athymic mice. In prior clinical Phase I trials of ci IUdR, the percentage IUdR-DNA incorporation in circulating granulocytes during and following the IUdR infusion as a surrogate for a proliferating normal human tissue (bone marrow) were measured by high pressure liquid chromatography (HPLC) and/or by flow cytometry. In general, the percentage IUdR-DNA incorporation in circulating granulocytes increased linearly with a linear increase in steady-state plasma levels of IUdR. Additionally, high 6%) % IUdR-DNA levels in peripheral granulocytes predicted for systemic bone marrow toxicity with ci IUdR in humans. In the pre-clinical studies of oral IPdR qd×14 d in athymic mice and ferrets, the percentage IUdR-DNA incorporation did not increase linearly with increasing daily po IPdR dosing, and was in circulating granulocytes following treatment, and importantly, no changes in blood counts seen in ferrets and rats, suggesting that bone marrow toxicity may not be dose-limiting for orally administered IPdR in humans. Indeed, in the toxicology studies of po IPdR daily×14-28 days in mice, rats, and ferrets, no myelosuppression was seen.

In human Phase I studies of ci IUdR, single tumor biopsies of high-grade gliomas, high-grade soft tissue sarcomas, H&N cancers, and liver metastases from colorectal cancers obtained at defined intervals during ci IUdR were used to correlate the % IUdR-DNA incorporation in tumor to steady-state drug levels. Again, a linear relationship of the % IUdR-DNA incorporation in tumor tissue and the steady-state plasma IUdR level was found.

The following examples are provided for illustration.

EXAMPLES

Example 1

A 32 year old female has a 12 cm soft tissue mass in the left pelvis. Biopsy reveals a high-grade soft tissue sarcoma.

The tumor is technically unresectable due to extension into the lumbosacral plexus, and RT is the mainstay of therapy and the only chance for cure. IPdR will be administered to the patient in the form of an oral drug (optimal dose of IPdR to be determined in ongoing clinical trials, predicted to be in the range of 0.1-50 gm/M2/day, preferably 2 to 5 gm/M2/day). The patient will undergo RT (typically, 70-80 Gy total dose delivered in 1.8-2.0 Gy fractions, 1 fraction/day, 5 days per week) 1-4 weeks (preferably 1-2 weeks, typically 1 week) following the initiation of IPdR. The patient will continue to take oral IPdR throughout the course of RT, and will discontinue IPdR following completion of RT. Given the radiation sensitizing effect of IPdR on tumor cells relative to normal tissue cells (i.e. increasing the therapeutic index (TI) of RT), maximum tumor control/eradication with minimal normal tissue toxicity will be achieved. This patient is expected to have an improved chance of survival at 2 years.

Example 2

A 58 year old male has a 6 cm mid-rectal mass with adjacent lymph node enlargement suggestive of N1 disease. Biopsy shows adenocarcinoma. The diagnosis is Stage III rectal cancer (adenocarcinoma), and standard-of-care therapy involves neoadjuvant (pre-surgery) chemotherapy and radiation (chemoRT), surgical resection, and potentially adjuvant (post-operative) chemotherapy. Neoadjuvant therapy is a critical component to this treatment regimen as it shrinks and sterilizes (kills cancer cells) the tumor as much as possible, and thus, optimizes the results of surgery. At the time of surgery, the resected tumor is examined pathologically, and if there is no evidence of residual viable tumor cells, the person is deemed to have a pathologic complete response (pCR). If pCR has been achieved, the 5-year disease-free survival (DFS) (considered equivalent to cure) rate is 85% vs 65% for those who do not achieve pCR. Furthermore, persons with a pCR do not require further (i.e. adjuvant) chemotherapy. In addition to the providing the mechanism for optimal (i.e. achieve pCR) surgery and its resultant improvement in disease-free and overall survival, neoadjuvant chemoRT also has the potential to lessen the morbidity of the surgical procedure by shrinking the tumor and thus requiring a less extensive resection (this may even obviate the need for a permanent colostomy in persons who would have required it if the surgery had been performed without neoadjuvant chemoRT).

The fluoropyrimidine class (FP) of chemotherapeutic agents including, 5-fluorouracil, floxuridine, capecitabine, and DPD-inhibiting fluoropyrimdines, is known to be effective in colorectal cancer treatment. FPs reduce a cell's ability to repair DNA damage, including the damage caused by RT. This effect is mediated through inhibition of thymidylate synthetase (TS), which then causes depletion/alteration of the nucleotide pools needed for DNA repair. The addition of IPdR further inhibits TS, with a greater than additive effect, as a result of the generation of intracellular IPdR monophosphate metabolite, IdUMP that further inhibits (by binding) TS leading to increased FP-mediated radiosensitization as well as enhancing IPdR-mediated radiosensitization. For rectal cancer, capecitabine is used in the neoadjuvant setting, with concomitant RT, and other FPs are used in adjuvant regimens (typically, 5-FU as part of a FOLFOX (foinic acid, 5-FU, oxaliplatin) regimen). The use of neoadjuvant capecitabine+RT allows a pCR in approximately 10-15% of Stage III rectal patients. The addition of IPdR to capecitabine+RT is predicted to increase the pCR rate from based on the IPdR+FP interactions and IPdR+IR interactions. Such an increase in the pCR rate should translate into a further improvement in 5-year DFS for patients with locally advanced rectal cancer.

IPdR will be given in conjunction with capecitabine+RT in the neoadjvant setting for a person with Stage III rectal cancer, with the goal of enhancing the degree of tumor reduction prior to surgery (improving the pCR (and thus, cure) rate and reducing the need for extensive (i.e. morbid) resection). Prior to the initiation of RT, IPdR will be administered to the patient in the form of an oral drug (optimal dose of IPdR to be determined in ongoing clinical trials, predicted to be in the range of 0.1-50 gm/M2/day, preferably 2 to 5 gm/M2/day). The patient will begin capecitabine therapy (typically, 750-875 mg/M2/dose bid) 1-4 weeks (preferably 1-2 weeks, typically 1 week) following the initiation of IPdR, and undergo RT (typically, 50.5 Gy total dose delivered in 1.8 Gy fractions, 5 days per week, for 28 fractions). The patient will continue to take oral IPdR in addition to capecitabine therapy throughout the course of RT, and will discontinue IPdR and capecitabine following completion of RT. The high therapeutic index of IPdR (minimal toxicity encountered at clinically effective dose), and specifically the lack of gastrointestinal toxicity and hand-foot syndrome (the dose limiting toxicities of capecitabine are gastrointestinal toxicity and hand-foot syndrome)) allows addition of IPdR, with its radiation sensitizing effect, to the capecitabine+RT regimen without the addition of significant toxicity.

Three to six weeks following completion of IPdR+capecitabine+RT, surgical resection will be performed. It is predicted that the synergistic radiation sensitizing effect of IPdR+capecitabine will enhance the pCR rate compared to capecitabine alone, so that more patients receiving IPdR+capecitabine+RT will achieve pCR. In this example, the patient will undergo non-radical (i.e. rectum-sparing, not requiring a permanent colostomy) resection, and pathology will reveal pCR, thus the patient will require no adjuvant chemotherapy, and will be expected to have a higher cure rate.

Example 3

A 62 year old male with a history of smoking has a 5 cm mass arising from the left tonsil, bilateral regional lymph node involvement and no evidence of distant metastatic disease (large primary tumor (>4 cm; T3), regional lymph node involvement (N3), and no distant metastases (M0) disease; typical of most head & neck cancers). Biopsy reveals squamous cell histology. As a result of his smoking habits, the patient demonstrates significant cardiac and pulmonary co-morbidities, rendering him high risk, and thus a poor candidate, for anesthesia and any extensive surgical procedure.

For cancers including those originating from the head & neck, gastrointestinal tract, genitourinary system, gynecologic system, lung and bone and soft tissue sarcomas, the platinum-based class (Pt) of chemotherapeutic agents including, but not limited to, cis-platin, carboplatin and oxaliplatin, is known to be effective. Administration of Pt agents produces intracellular Pt-DNA adducts in these tumors that are then unable to appropriately repair the additional DNA damage caused by RT. The addition of IPdR (IUdR) produces unique IU:Pt adducts in DNA, enhancing Pt cytotoxicity and greater than additive (i.e. synergistically) enhancement of the individual RT-sensitizing effects of Pt agents and IPdR (IUdR).

Given the patient's high risk for surgery, his treatment plan will involve a combination of chemotherapy and definitive RT (for those patients who are surgical candidates, a lower, neoadjuvant (i.e. pre-operative) dose of RT would be administered). Prior to the initiation of RT, IPdR will be administered to the patient in the form of an oral drug (optimal dose of IPdR to be determined in ongoing clinical trials, predicted to be in the range of 0.1-50 gm/M2/day, preferably 2 to 5 gm/M2/day). After one week of IPdR therapy, the patient will begin cis-platin (100 mg/M2 IV on days 1, 22 and 43 or 40-50 mg/M2 q week×6-7 weeks) and RT (definitive dose, total dose: 66-74 Gy administered in 2.0 Gy fractions, 1 fraction/day, 5 days/week×6-7 weeks). Cis-platin and IPdR will be discontinued following completion of RT. The high therapeutic index of IPdR (minimal toxicity encountered at clinically effective dose), and specifically the lack of renal toxicity, ototoxicity, peripheral neuropathy and myelosuppression (i.e. will not augment the dose limiting toxicities of cis-platin (renal toxicity, ototoxicity, peripheral neuropathy and myelosuppression)), allows addition of IPdR, with its radiation sensitizing effect, to the cis-platin+RT regimen without the addition of significant toxicity.

Following completion of IPdR+cis-platin+RT, physical examination and imaging evaluation indicate no evidence of residual tumor, i.e. a clinical complete response (cCR). cCR is the goal of chemotherapy+definitive RT, as it obviates the need for surgery to remove residual tumor. Here, the patient is spared the high risk of surgery to render him free of residual tumor. A patient who receives cis-platin+definitive RT and achieves a cCR has a cure rate of approximately 60%. The addition of IPdR to cis-platin+definitive RT results in enhancement of cytotoxicity on the basis of both drug-drug (i.e. IPdR—Pt) and drug-drug-RT (IPdR—Pt-RT) interactions, and would be predicted to further improve the patient's cure rate.

Example 4

A 37 year old male presents with headache and a seizure. MRI reveals a 4 cm enhancing lesion in the left cerebral cortex with areas of hemorrhage, peritumoral edema and lack of calcification. No additional intraparemchymal lesions are noted. Biopsy reveals a glioblastoma multiforme (GBM), and molecular analysis of the tumor cells reveals MGMT promoter methylation.

For specific cancers originating from the central nervous system and bone and soft tissue sarcomas, methylating agents (MA) including, temozolomide (TMZ) and the nitrosoureas are known to be effective. Specifically, in high-grade gliomas with MGMT promoter methylation (up to 40% of patients), TMZ produces an additive biochemical enhancement of RT cytotoxicity. Clinical trials have demonstrated a 5-month survival benefit for the addition of TMZ to RT for patients with MGMT promoter methylated high-grade gliomas (from 10 months to 15 months), and so it is considered the standard-of-care, but virtually all patients will recur within the same area of the brain. However, randomized Phase 3 clinical trials show no survival benefit to TMZ+RT vs RT alone in GBM patients whose tumors possess an unmethylated MGMT promoter (60% of all GBM patients). TMZ is administered with RT even for these unmethylated MGMT high-grade gliomas because it is well tolerated and survival after RT alone is so dismal that TMZ is given with the hope of deriving some, albeit statistically insignificant, benefit.

Clinical trials of continuous infusion (ci) IUdR+RT for patients with high-grade gliomas demonstrated a prolongation of survival of greater than 50% compared to RT alone (Table 1). This survival benefit of ci IUdR+RT compared to TMZ+RT is predicted based on the molecular interactions of TMZ+RT, which are only additive, compared to the molecular interactions of IUdR+RT, which are greater than additive (i.e. synergistic). Furthermore, the radiosensitizing effect of IUdR (IPdR) is independent of MGMT promoter methylation status, so it is useful across the molecular spectrum of high-grade gliomas. Although not routinely analyzed, deficiencies in MMR and BER mechanisms have been documented in many high-grade gliomas, and tumors with these defects would be expected to derive even greater benefit from the addition of IPdR to their RT regimen.

The patient will initially undergo maximal surgical resection, with a goal of <5% residual disease (the infiltrative nature of high-grade gliomas dictates this goal). Prior to the initiation of RT, IPdR will be administered to the patient in the form of an oral drug (optimal dose of IPdR to be determined in ongoing clinical trials, predicted to be in the range of 0.1-50 gm/M2/day, preferably 2 to 5 gm/M2/day). The patient will begin TMZ therapy (75-150 mg/M2/day)+RT (typically, 60 Gy delivered in 2 Gy fractions, 1 fraction/ day, 5 days/week×6 weeks) one week following the initiation of IPdR. The high therapeutic index of IPdR (minimal toxicity encountered at clinically effective dose), and specifically the lack of bone marrow suppression (i.e. will not augment the dose limiting toxicity of TMZ (bone marrow suppression)), allows addition of IPdR, with its radiation sensitizing effect, to the TMZ+RT regimen without the addition of significant toxicity. The patient will continue TMZ and IPdR throughout the course of RT. At the conclusion of RT, IPdR will be discontinued, and the patient will proceed with TMZ on a new, maintenance dosage schedule (typically 150 mg/M2/day, days 1-5 of a 28-day cycle, for 6 cycles).

The radiosensitizing effect of IPdR, in addition to the enhancement of RT effect with TMZ in this MGMT promoter methylated GBM, will optimize tumor control/eradication for this patient, and prolongation of survival (e.g., by up to 70%, 24 months) is predicted.

Example 5

A 57 year old female has a 5 cm mass in the head of the pancreas with obstruction of the common bile duct and tumor encasing the superior mesenteric artery, rendering the tumor initially unresectable. No evidence of metastatic disease is seen. This scenario occurs in up to 35% of patients diagnosed with pancreatic cancer (approximately 28,000 patients/year in the U.S.). Clinical trials in such patients with locally advanced pancreas cancer have recently focused on combinations of chemotherapy+RT to shrink the tumor enough that it becomes resectable. Such a tumor downstaging occurs in approximately 25% of patients.

Ribonucleotide reductase (RR) is an enzyme critical to a cell's recovery from DNA damage caused by RT. RR is principally responsible for maintaining nucleotide pool balance and the DNA replication process that is needed to repair RT-induced DNA damage. Ribonucleotide reductase inhibitors (RRI) including hydroxyurea, gemcitabine, triapine and COH29, function as radiation sensitizers by altering the nucleotide pool composition and inhibiting repair of RT-induced DNA damage. The addition of IPdR to RRI administration causes further inhibition of DNA damage repair, in a synergistic (i.e. greater than additive) manner. Gemcitabine (2',2'-difluoro-2'-deoxycitidine, dFdc) is a cytidine analog and an active chemotherapy drug in patients with metastatic pancreas cancer. It is a prodrug that requires cellular uptake and intracellular phosphorylation to gemcitabine di- and triphosphates (dFdCDP and dFdCTP, respectively), which are the active drug metabolites. dFdCTP potentially inhibits RR and is believed to be a mechanism for radiosensitization as previously described.

In this example, IPdR will be given in conjunction with gemcitabine+RT with the goal of enhancing the degree of tumor reduction to make it amenable to surgical resection. Prior to the initiation of RT, IPdR will be administered to the patient in the form of an oral drug (optimal dose of IPdR to be determined in ongoing clinical trials, predicted to be in the range of 0.1-50 gm/M2/day, preferably 2 to 5 gm/M2/day). The patient will begin gemcitabine therapy (typically, 1000 mg/M2/dose IV q week) 1-4 weeks (preferably 1-2 weeks, typically 1 week) following the initiation of IPdR, and undergo RT (typically, 54 Gy total dose delivered in 1.8 Gy fractions, 1 fraction/day, 5 days per week). The patient will continue to take oral IPdR in addition to receiving gemcitabine therapy throughout the course of RT, and will discontinue IPdR following completion of RT. The high therapeutic index of IPdR (minimal toxicity encountered at clinically effective dose), and specifically the lack of myelosuppression (the dose limiting toxicity of gemcitabine) allows addition of IPdR, with its radiation sensitizing effect, to the gemcitabine+RT regimen without the addition of significant toxicity. Further inhibition, by IPdR, of repair of RT-induced DNA damage resulting from RRI+RT therapy will optimize tumor control/eradication.

The patient's CT scan post-IPdR+gemcitabine+RT shows that it is technically resectable, and upon pathologic inspection, the margins are free of tumor (i.e. a R0-resection), a scenario that occurs in up to 40% of patients who undergo resection following RT-induced downstaging, with these patients' median survival approaches 2 years compared to less than 1 year for patients who remain unresectable following RT. Given the preclinical data combining IUdR (or IPdR)+RRI (e.g. gemcitabine)+RT, the drug-drug and drug-drug-RT greater than additive interactions of this combination would be expected to further increase the percentage of patients that are able to achieve an R0-resection (e.g., from 40% to >60%).

Example 6

A 60 year old male non-smoker has a 6 cm distal esophagus mass. Biopsy reveals a squamous cell cancer, and immunohistochemical analysis of the specimen reveals reduced expression of the base excision repair (BER) enzyme, MYH, and increased 8-oxoguanine oxidative damage in tumor compared to normal esophagus, suggesting a BER-deficient cancer resulting from chronic gastric reflux injury. Clinically, BER-deficient tumors are aggressive, often with regional lymph node involvement. Evaluation demonstrates that this patient has Stage 3B disease, and the treatment plan will include chemotherapy, RT and surgery, with an expected 5-years survival rate of 20%. Complete surgical resection is imperative for cure, and so neoadjuvant therapy is administered with the goal of downstaging the patient's disease and rendering the tumor more amenable to resection.

In this example, IPdR will be given in conjunction with cis-platin+5-FU+RT with the goal of enhancing the degree of tumor reduction to allow surgical resection. Prior to the initiation of RT, IPdR will be administered to the patient in the form of an oral drug (optimal dose of IPdR to be determined in ongoing clinical trials, predicted to be in the range of 0.1-50 gm/M2/day, preferably 2 to 5 gm/M2/day). The patient will begin cis-platin therapy (typically, 100 mg/M2/dose IV on days 1 and 29) and continuous infusion 5-FU (1000 mg/M2/day, days 1-4 and 29-32) 1-4 weeks (preferably 1-2 weeks, typically 1 week) following the initiation of IPdR, and undergo RT (typically, 50.4 Gy total dose delivered in 1.8 Gy fractions, 1 fraction/day, 5 days per week). The patient will continue to take oral IPdR throughout the course of RT, and will discontinue IPdR following completion of RT. The high therapeutic index of IPdR (minimal toxicity encountered at clinically effective dose), and specifically, the lack of renal toxicity, ototoxicity, peripheral neuropathy, myelosuppression and gastrointestinal toxicity (the dose limiting toxicities of cis-platin+5-FU) allows addition of IPdR, with its radiation sensitizing effect, to the cis-platin+5-FU+RT regimen without the addition of significant toxicity.

The addition of IPdR to the standard regimen would exploit the BER-deficiency of the patient's tumor for therapeutic benefit. Based on the preclinical data, the BER-deficiency would result in increased IUdR-DNA incorporation in the tumor cells because they would be less able to repair the G:IU adducts. This augmentation of response would be in addition to the known greater than additive drug-drug interactions, IUdR (IPdR)+cis-platin and IUdR (IPdR)+5-FU (via IdUMP binding (inhibiting) thymidylate synthase, as well as the IUdR (IPdR)+RT synergism. This augmentation of response would be predicted to result in greater tumor reduction, and thus increasing the likelihood of complete surgical resection, culminating in improved survival.

Example 7

A 38 year old female, non-smoker, presents with a persistent cough and chest x-ray reveals a 6 cm right upper lung mass. Further evaluation and biopsy demonstrate a Stage 3B (T3 N3 M0) adenocarcinoma of the lung. Molecular testing of the tumor shows no mutations in the ALK or EGFR genes, but does reveal promoter methylation of hMLH1, a MMR gene (i.e. MMR-deficient tumor). MMR deficiency is present in approximately 50% of lung cancers in never smokers, and is associated with a poor prognosis.

Standard-of-care for this patient is either cis-platin+ etoposide+RT or RT alone. The poor response of MMR-deficient tumors compared to those that are MMR-proficient can be predicted on the basis of the MMR-deficiency because these tumors have been shown to be "damage-tolerant" (i.e. resistant) to the specific DNA damage caused by cytotoxic chemotherapy and ionizing radiation (IR). IUdR-mediated radiosensitization results from the formation of G:IU DNA adducts that, once generated, are also tolerated by MMR-deficient tumors. The administration of po IPdR generates a 2-3-fold increase in IUdR-DNA incorporation compared to the administration of ci IUdR, enhancing the degree of radiosensitization and overcoming the resistance mechanisms used by MMR-deficient tumors. Thus, the addition of IPdR to a chemotherapy and/or RT regimen would be expected to augment tumor response in MMR-deficient tumors. In this example, prior to the initiation of RT, IPdR will be administered to the patient in the form of an oral drug (optimal dose of IPdR to be determined in ongoing clinical trials, predicted to be in the range of 0.1-50 gm/M2/day, preferably 2 to 5 gm/M2/day). The patient will begin cis-platin therapy (typically, 50 mg/M2/dose IV on days 1, 8, 29 and 36) and etoposide (50 mg/M2/day, days 1-5 and 29-33) 1-4 weeks (preferably 1-2 weeks, typically 1 week) following the initiation of IPdR, and undergo RT (typically, 60 Gy total dose delivered in 2 Gy fractions, 1 fraction/day, 5 days per week). The patient will continue to take oral IPdR throughout the course of RT, and will discontinue IPdR following completion of RT. The high therapeutic index of IPdR (minimal toxicity encountered at clinically effective dose), and specifically, the lack of renal toxicity, ototoxicity, peripheral neuropathy, myelosuppression and gastrointestinal toxicity (the dose limiting toxicities of cis-platin+etoposide) allows addition of IPdR, with its radiation sensitizing effect, to the cis-platin+etoposide+RT regimen without the addition of significant toxicity. The expectation would be improved tumor control with this regimen compared to the identical regimen without the addition of IPdR. Furthermore, if, for any reason, a patient with such an MMR-deficient tumor receives RT alone (as opposed to chemotherapy+RT), the addition of IPdR to the RT regimen would be expected to produce similar, improved results.

Example 8

Hypofractionated RT using stereotactic radiosurgery technique. A 75 year old female smoker is diagnosed with a 4 cm T2 N0 M0 squamous cell carcinoma of the lung. Although surgical resection would provide the best chance for cure, the patient has severe chronic obstructive pulmonary disease as a consequence of her smoking habits, and is not a candidate for surgery.

This patient will be treated with RT alone, specifically using a stereotactic radiosurgery (SRS) technique, where the total dose of RT is administered over a short timeframe (typically 1-14 days) in a limited number (typically 1-5) of doses, with each dose delivering a large IR fraction (typically, 8-20 Gy). Stereotactic techniques are appropriate for small (typically, <5 cm) primary lung tumors or lung metastases away from central structures (e.g. trachea, bronchus and heart). If RS is administered at full dose (50-60 Gy), primary lung tumors demonstrate an up to 80% response rate without excessive normal tissue toxicity. In this example, the central location of the patient's tumor dictates that parts of the esophagus, trachea, bronchus and heart will be in the SRS field, thus limiting the dose to (40 Gy total dose, delivered as 8 Gy fractions, 5 fractions administered over 14 days), and thereby also compromising response rate, which under these circumstances is expected to be 50%. The patient in this example will receive, prior to the initiation of SRS, IPdR in the form of an oral drug (optimal dose of IPdR to be determined in ongoing clinical trials, predicted to be in the range of 0.1-50 gm/M2/day, preferably 2 to 5 gm/M2/day). One-four weeks (preferably 1-2 weeks, typically 1 week) following the initiation of IPdR, the patient will undergo SRS. The patient will continue to take oral IPdR throughout the course of SRS, and will discontinue IPdR following completion of SRS. The high therapeutic index of IPdR (minimal toxicity encountered at clinically effective dose), and specifically, the lack of cardiac or mucosal toxicities, allows addition of IPdR, with its radiation sensitizing effect, to the SRS regimen without the addition of significant toxicity. Based on IPdR's RT enhancement ratio of 1.3-6.0 as determined in preclinical studies, this patient's response rate would be predicted to improve.

The addition of IPdR to SRS regimens is especially valuable because these are situations in which RT is typically the only treatment aimed at local tumor control. Other examples of these situations include (lesions typically must be <5 cm) primary of metastatic liver tumors, and primary or metastatic brain and spinal cord tumors. The radiosensitization effect (1.3-6.0×) of IPdR is predicted to enhance the effectiveness of SRS techniques to a clinically significant degree.

Example 9

A 27 year-old female presents with a chordoma arising from the base of the skull (BOS). Chordomas are low-grade malignancies with low metastatic potential, and although the clinical course is slow (i.e. years), local progression and recurrence following resection occur in the majority of patients. Surgical resection is critical, but almost always limited by their critical location (i.e. arising from notochord remnants, chordomas inherently involve critical neurological structures) and infiltration into adjacent bone. To overcome the potential evolution of residual disease, RT is used in the postoperative setting. Chordomas respond best to high doses (in the range of 70 Gy) of radiation, but these tumors represent a challenge for RT because nearby critical neurologic structures (spinal cord, brainstem, and optic pathways) limit the doses that can be delivered. Charged particles, namely protons, have been used in addition or instead of photons for their distinct advantage over conventional RT because of the superior dose distribution due to the rapid radiation fall-off beyond the target. For BOS chordomas, proton therapy (PT) is the adjuvant (i.e. post-surgical resection) treatment of choice, with doses in the range of 60-95 Gy equivalent. The highest doses of PT are, predictably, associated with greater rates of tumor control, but at the expense of toxicity to surrounding vital neurological structures. The mechanism of cytotoxicity from PT is identical to that of conventional RT, i.e. IR-induced DNA damage, therefore, the radiosensitization effect of IPdR would be predicted to apply when administered in conjunction with PT.

The patient will receive, prior to the initiation of PT, IPdR in the form of an oral drug (optimal dose of IPdR to be determined in ongoing clinical trials, predicted to be in the range of 0.1-50 gm/M2/day, preferably 2 to 5 gm/M2/day). One-four weeks (preferably 1-2 weeks, typically 1 week) following the initiation of IPdR, the patient will undergo PT (total dose 60-95 Gy-equivalent, 1.8-3.5 Gy-equivalent fractions, 1 fraction/day, 5 fractions/week). The patient will continue to take oral IPdR throughout the course of PT, and will discontinue IPdR following completion of PT. The high therapeutic index of IPdR (minimal toxicity encountered at clinically effective dose), and specifically, the lack of neurologic toxicity, allows addition of IPdR, with its radiation sensitizing effect, to the PT regimen without the addition of significant toxicity. Based on IPdR's RT enhancement ratio of 1.3-6.0 as determined in preclinical studies, local control and overall survival is predicted to improve in this patient.

PT as a modality of RT is gaining popularity as it allows delivery of higher doses of IR with equivalent or less toxicity (i.e. the TI of PT is higher than that of conventional RT). The use of PT, however, is limited by availability (limited number of PT centers), feasibility (logistics involved in the administration of PT formidable), and the cost (cost of PT is, on average, 3-5 times the cost of conventional RT). The obstacles of PT justify its use in cases where higher RT doses represent the best, and often only, chance for survival, and in those cases, the addition of IPdR (with it's predicted radiosensitization) to PT is predicted to result in significant therapeutic benefit (i.e. increases the TI of the IR by up to 1.5×).

Example 10

Therapeutic Index (TI) is an important concept in considering the utility of a drug in clinical practice. In general, TI is a quantitative relationship between the safety (toxicology) of a drug and its efficacy (pharmacology). A drug's TI is a ratio between two doses, the dose of the drug that causes adverse effects at an incidence/severity not compatible with the targeted indication divided by the dose that leads to the desired pharmacological effect, and the value of the TI is dependent upon the choice of doses used to calculate the ratio. TI is a useful concept for comparing different drugs used in the same situation, wherein identical requirements for efficacy and toxicity can be applied to both drugs. TI is also useful as a semi-quantitative measure, wherein a drug is demonstrated to have a low vs high TI, with higher TI being desirable.

In the case of IPdR (IUdR), it is appropriate to consider the TI in terms of % IUdR-DNA cellular incorporation. Preclinical studies have confirmed and quantified the direct relationship between the dose of IPdR administered and the % IUdR-DNA cellular incorporation, so the % incorporation may be used for TI calculations in place of the actual dose of IPdR:

$$TI_{IPdR} = \frac{\% \, IUdR-DNA \text{ cellular incorporation in tumor cells}}{\% \, IUdR-DNA \text{ cellular incorporation in normal tissue cells}}$$

Using this formula, the TI of ci IUdR in the clinical studies (Tables 1 and 2) is calculated using the values (% IUdR-DNA incorporation) at which grade 3 or 4 (i.e. dose limiting) toxicities (myelosuppression, gastrointestinal and hepatic) were encountered, revealing a TI approximately equal to 1:

$$TI_{ciIUdR} = \frac{3-8\%}{4-6\%} \cong 1$$

Although the $TI_{ci\,IUdR}$ in these studies was relatively low, ci IUdR at these doses did enhance tumor control in typically "radioresistant" (poorly RT-responsive) tumors, including glioblastoma multiforme (GBM) and high-grade sarcomas.

From the preclinical studies using human tumor xenografts, (MMR+ colorectal cancers and GBM), the following $TI_{ci\,IUdR}$ can be calculated:

$$TI_{ciIUdR} = \frac{2-4\%}{3-5\%} \approx \leq 1$$

(ci IUdR×6-14 days; GI toxicity of >20% body weight loss) and:

$$TI_{poIPdR} = \frac{4-6\%}{1-2\%} \cong 2-6$$

(po IPdR×14 days; no myelosuppression and <10% body weight loss).

Example 11

The observed $TI_{po\,IPdR}$ seen in the initial Phase I and II clinical trials of po IPdR in Example 10 will be confirmed.

In the ongoing clinical trial of po IPdR in patients with gastrointestinal cancers (including patients with metastases), a tumor biopsy will be obtained following 7-28 days of po IPdR (dose of IPdR to be determined in ongoing clinical trials, predicted to be in the range of 0.1-50 gm/M2/day, preferably 2 to 5 gm/M²/day) (i.e. prior to the initiation of RT, which is anticipated to begin 7-28 days following the initiation of po IPdR). Tumor biopsies are obtained prior to RT to eliminate any cytotoxic effect of IR on the tumor in the analyses of % IUdR-DNA cellular incorporation. Samples of normal tissues including circulating granulocytes (as a surrogate of bone marrow) and oral mucosal scrapings (as a surrogate of gastrointestinal tract) will be obtained at the same time (i.e. prior to the initiation of RT) and also at weekly intervals throughout IPdR+RT. The cells obtained at these times will be analyzed for % IUdR-DNA cellular incorporation, and the values used to calculate the TI.

Example 12

Attempt to further increase the TI of po IPdR by altering the "loading" schedule of po IPdR prior to the initiation of RT.

a. Administration of po IPdR TID×7 days before the initiation of RT. Based on the plasma pharmacokinetics of po IPdR (i.e. peak plasma levels of the IUdR (active drug) >4 μM×4 hours following a po IPdR dose of 2400 mg, with IUdR levels decreasing to 1 μM over 8 hours), a TID dosing schedule (as compared to once QD) will more closely mimic the ci IUdR exposure (steady state plasma concentration of 1 μM) that produced clinical responses in the clinical studies of ci IUdR (Tables 1 and 2).

PO IPdR (dose of IPdR to be determined in ongoing clinical trials, predicted to be in the range of 0.1-50 gm/M2/day divided into 3 equal doses, preferably 2 to 5 gm/M²/day) will be administered prior to the initiation of RT (7 days following the initiation of po IPdR). A tumor biopsy will be obtained immediately prior to the initiation of RT (i.e. following 7 of po IPdR). Samples of normal tissues including circulating granulocytes (as a surrogate of bone marrow) and oral mucosal scrapings (as a surrogate of gastrointestinal tract) will be obtained at the same time (i.e. prior to the initiation of RT) and also at weekly intervals throughout IPdR+RT. The cells obtained at these times will be analyzed for % IUdR-DNA cellular incorporation, and the values used to calculate the TI of the TID dosing administration schedule of IPdR.

b. Administration of po IPdR QD×14-28 days before the initiation of RT. Based on the plasma pharmacokinetics of po IPdR (i.e. peak plasma levels of the IUdR (active drug) >4 μM×4 hours following a po IPdR dose of 2400 mg, with IUdR levels decreasing to 1 μM over 8 hours), a prolonged exposure (i.e. 14-28 days compared to 7 days) to po IPdR will more closely mimic the ci IUdR exposure that produced clinical responses in the clinical studies of ci IUdR (Tables 1 and 2).

PO IPdR (dose of IPdR to be determined in ongoing clinical trials, predicted to be in the range of 0.1-50 gm/M2/day, preferably 2 to 5 gm/M²/day) will be administered prior to the initiation of RT, to begin 14-28 days following the initiation of po IPdR. A tumor biopsy will be obtained immediately prior to the initiation of RT (i.e. following 14-28 days of po IPdR). Samples of normal tissues including circulating granulocytes (as a surrogate of bone marrow) and oral mucosal scrapings (as a surrogate of gastrointestinal tract) will be obtained at the same time (i.e. prior to the initiation of RT) and also at weekly intervals throughout IPdR+RT. The cells obtained at these times will be analyzed for % IUdR-DNA cellular incorporation, and the values used to calculate the TI of the TID dosing administration schedule of IPdR.

Comparison will then be made between the calculated TIs, using % IUdR-DNA cellular incorporation levels, for po IPdR administered via the three different dosing (i.e. "loading") schemes:

QD dosing for 7 days vs
QD dosing for 14-28 days vs
TID dosing for 7 days
prior to the initiation of RT.

Example 13

In conjunction with the calculation and comparison of the TIs of po IPdR administered via three different dosing schedules in Example 12 above, for each of the dosing regimes, prediction of the sensitizer enhancement ratio (SER) in tumor will be made by measuring the proportion of IUdR-DNA labeled (vs unlabeled) tumor cells by flow cytometry.

The degree of IPdR-mediated radiosensitization is directly related to the % IUdR-DNA cellular incorporation, and because intracellular IdUTP pools are available for IUdR-DNA incorporation only during the S-phase (DNA synthesis phase) of the cell cycle, the number of unlabeled cells must be minimized for maximal radiosensitization. Experimental and mathematical work has derived and validated the following formula to calculate the SER:

$$\text{Tumor } SER = 1 + \frac{-\log_{10}(\text{proportion of unlabeled cells})}{\log_{10}(\text{total number of viable cells})}.$$

Using the previously described flow cytometry techniques with anti-IUdR antibodies, analyses of single cell aliquots of the tumor biopsy specimens (obtained immediately prior to the initiation of RT, following 7-28 days of po IPdR) will be used for the calculations of Tumor SERs.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

It should be understood that the order of steps or order for performing certain actions is immaterial so long as the present teachings remain operable. Moreover, two or more steps or actions may be conducted simultaneously.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

TABLE 1

NCI sponsored clinical efficacy studies of IUdR (compared to contemporary historical RT-alone controls) for treatment of high-grade primary brain tumors (RTOG*, NCI** trials)

| Tumor | Treatment | Median survival (Months) |
|---|---|---|
| Anaplastic astrocytomas (Grade 3 of 4)* | RT alone | 24 |
| | RT + IUdR | 39 |
| Glioblastoma Multiforme (Grade 4 of 4)** | RT alone | 9 |
| | RT + IUdR | 15 |

TABLE 2

Clinical efficacy studies of IUdR (compared to historical RT-alone controls) for treatment of high-grade sarcomas (NCI; University of Michigan* trials)

| Tumor | Treatment | Local Control at 2 years |
|---|---|---|
| High grade sarcomas (resectable)*** | RT + Surgery | 25% |
| | RT + IUdR + Surgery | 45% |
| High grade sarcomas (un-resectable)** | RT alone | <10% |
| | RT + IUdR | 60% |

TABLE 3

Summary of IPdR pre-clinical studies leading to IND application and initial clinical Phase 0 trial

| Study | Description | Summary of Findings |
|---|---|---|
| A. IPdR Metabolism by hepatic aldehyde oxidase | | |
| Chang, 1992 | Metabolism of IPdR vs IUdR | Elucidated IPdR metabolism by aldehyde oxidase Characterized properties of aldehyde oxidase |
| Kinsella, 1998, 2000, 2008 | IPdR Metabolism in rats and ferrets and in human tissues | Characterized kinetics of IPdR metabolism |

TABLE 3-continued

Summary of IPdR pre-clinical studies leading to IND application and initial clinical Phase 0 trial

| Study | Description | Summary of Findings |
|---|---|---|
| B. Pharmacokinetic and toxicology studies | | |
| Kinsella, 1994, 1998, 2000 | Pharmacokinetics of po IPdR in mice | Established absorption, distribution, metabolism, and elimination kinetics of po IPdR in mice |
| Kinsella, 2000 | Pharmacokinetics (PK) and toxicity/toxicology of IPdR in ferrets (po) and rhesus monkeys (iv) | Established distribution, metabolism, and elimination kinetics of IPdR in non-rodent species. Noted mild weight loss at highest dose; but no significant hematologic, biochemical, or histopathologic changes |
| Kinsella, 2008 | Pharmacokinetics and toxicity/toxicology of po IPdR in Fischer rats | Established IPdR and IUdR concentration-time profiles Reported HPLC/tandem mass spectroscopy methods for plasma IPdR and IUdR levels. |
| Kummar, 2013 | Pharmacokinetics of single-dose po IPdR in humans | Phase 0 study of po IPdR, 150 mg-2400 mg in humans: No toxicities. |
| C. Pre-clinical efficacy studies of IPdR-mediated radiosensitization | | |
| Kinsella, 1998, 2000 Seo, 2004, 2005 | Efficacy/toxicity studies of po IPdR vs ci IUdR using human colorectal and glioblastoma tumor xenografts. | Increased IUdR-DNA incorporation in tumors; decreased in normal tissues, po IPdR vs ci IUdR. 1.3-1.5 fold enhancement of response to RT with po IPdR |
| Kinsella, 1994 | Efficacy, PK, toxicity, and DNA incorporation of po IPdR vs po IUdR in human colon cancer xenografts. | Demonstrated improved therapeutic index of po IPdR vs po IUdR for IUdR-mediated radiosensitization |

What is claimed is:

1. A method of treating a human patient having cancer, the method comprising:
   administering 5-iodo-2-pyrimidinone-2'-deoxyribose (IPdR) to the patient in the form of an oral drug;
   administering a chemotherapeutic drug to the patient; and,
   administering radiation therapy to the patient;
   wherein the IPdR is administered at least for a period of time prior to the administering radiation therapy to the patient; and
   wherein a base excision repair (BER) inhibitor is not administered to the patient prior to the administering radiation therapy to the patient.

2. The method of claim 1, wherein the administering radiation therapy to the patient comprises administering radiation therapy using a hyperfractionated technique.

3. The method of claim 1, wherein the patient cannot tolerate an optimum radiation therapy field without the administering IPdR to the patient.

4. The method of claim 1, wherein the administering radiation therapy to the patient comprises administering radiation therapy using at least one technique selected from the group consisting of 3-dimensional conformal radiation therapy, intensity-modulated radiation therapy, image-guided radiation therapy, tomotherapy, stereotactic radiosurgery, and stereotactic body radiation therapy.

5. The method of claim 1, wherein a source of radiation therapy is selected from the group consisting of protons and carbon ions.

6. The method of claim 1, wherein the cancer is mismatch repair (MMR)-deficient.

7. The method of claim 1, wherein the administering a chemotherapeutic drug to the patient comprises administering the chemotherapeutic drug at least for a period of time prior to the administering radiation therapy to the patient.

8. The method of claim 1, wherein the chemotherapeutic drug is selected from the group consisting of a fluoropyrimidine, a platinum analog, a ribonucleotide reductase inhibitor, and a methylating agent.

9. The method of claim 1, wherein the administering IPdR to the patient comprises administering IPdR at a dose of 0.1 to 50 gm/$M^2$/day.

10. The method of claim 1, wherein the chemotherapeutic drug is temozolomide (TMZ).

11. The method of claim 10, wherein the IPdR and the temozolomide (TMZ) are administered contemporaneously.

12. The method of claim 1, wherein the chemotherapeutic drug is temozolomide (TMZ) and wherein the cancer is brain cancer.

13. The method of claim 1, wherein the chemotherapeutic drug is a fluoropyrimidine.

14. The method of claim 13, wherein the IPdR and the fluoropyrimidine are administered contemporaneously.

15. The method of claim 1, wherein the chemotherapeutic drug is a fluoropyrimidine and wherein the cancer is gastrointestinal cancer.

* * * * *